US005843689A

United States Patent [19]

Anderson

[11] Patent Number: 5,843,689
[45] Date of Patent: Dec. 1, 1998

[54] METHOD FOR THE ASSESMENT OF THE MONONUCLEAR LEUKOCYTE IMMUNE SYSTEM

[76] Inventor: Jeffrey E. Anderson, 2245 N. Dayton, Chicago, Ill. 60614

[21] Appl. No.: 856,230

[22] Filed: May 14, 1997

Related U.S. Application Data

[63] Continuation of Ser. No. 406,381, Mar. 17, 1995, Pat. No. 5,656,446, which is a continuation of Ser. No. 144,481, Sep. 9, 1993, Pat. No. 5,445,939, which is a continuation of Ser. No. 751,620, Oct. 28, 1991, abandoned, which is a continuation of Ser. No. 415,905, Oct. 2, 1989, abandoned, which is a continuation of Ser. No. 895,754, Aug. 12, 1986, abandoned.

[51] Int. Cl.$^6$ .............................. G01N 33/53; C12Q 1/02
[52] U.S. Cl. .............................. 435/7.24; 435/29; 435/39
[58] Field of Search ................................ 435/7.24, 29, 39

[56] References Cited

U.S. PATENT DOCUMENTS

| | | |
|---|---|---|
| 4,284,412 | 8/1981 | Hansen et al. . |
| 4,381,295 | 4/1983 | Kung et al. . |
| 4,492,752 | 1/1985 | Hoffman . |
| 4,520,110 | 5/1985 | Stryer et al. . |
| 4,599,304 | 7/1986 | Lanier et al. . |
| 4,607,007 | 8/1986 | Lainer et al. . |
| 4,677,061 | 6/1987 | Rose et al. . |
| 4,701,408 | 10/1987 | Koestler et al. . |
| 4,727,020 | 2/1988 | Recktenwald . |
| 4,778,750 | 10/1988 | Gottlieb . |
| 5,656,446 | 8/1997 | Anderson ............................. 435/7.24 |

OTHER PUBLICATIONS

Ashman, Robert F., "Fundamental Immunology," *Lymphocyte Activation*, 267 (Ed. W. Paul, 1984).
Bach et al., "The Use of Monoclonal Anti–T Cell Antibodies to Study T Cell Imbalances in Human Diseases," *Clin. Exp. Immunol.*, 45:449 (1981).
Bernard and Baumsell, "The Clusters of Differentiation (CD) Defined by the First International Workshop on Human Leucocyte Differentiation Antigen," *Human Immunology*, 11:1 (1984).
Bettens et al., "Effects of Cyclosporin–A on the Early Activation of Human T Helper Lymphocytes: Inhibition of RNA–Synthesis and Modification of the Expression of Activation Antigens," *Immunobiol.*, 170:434 (Dec. 1985).
Blue et al., "Coexpression of T4 and T8 on Peripheral Blood T Cells Demonstrated by Two–Color Fluorescence flow Cytometry," *J. Immuno.*, 134:2281 (Apr., 1985).
Cantrell et al., "Transient Expression of Interleukin 2 Receptors, Consequences of T Cell Growth," *J. Exp. Med.*, 158:1895 (1983).
Carney et al. I, "Functional Properties of T Lymphocytes and Their Subsets In Cytomegalovirus Mononucleosis," *J. Immuno.*, 130:1 (Jan., 1983).
Carney et al. II, "Analysis of T Lymphocyte Subsets in Cytomegalovirus Mononucleosis," *J. Immuno.*, 126:6 (Jun., 1981).

Chouaib et al., "The Mechanism of Inhibition of Human IL2 Production," *J. Immuno.*, 2463 (1982).
Damle et al., "Immunoregulatory T Cell Circuits in Man," *J. Immuno.*, 134:235 (Jan., 1985).
Depper et al. I, "Blockade of the Interleukin–2 Receptor By Anti–Tac Antibody: Inhibition of Human Lymphocyte Activation," *J. Immuno.*, 131:690 (1983).
Deppler et al I, "Interleukin 2 (IL–2) Augments Transcription of the IL–2 Receptor Gene," *Proc. Natl. Acad. Sci. U.S.A.*, 82:4230 (Jun., 1985).
Dillman et al., "Statistical Approach to Immunosuppression Classification Using Lymphocyte Surface Markers and Functional Assays," *Cancer Res.*, 43:417 (1983).
Dudrhiri, "Mechanism of Accessory Cell Requirement In Inducing IL2 Responsiveness by Human T3 Lymphocytes That Generate Colonies Under PHA Stimulation," *J. Immuno.*, 135:1813 (Sep., 1985).
Ebert et al., "Diminished Interleukin 2 Production and Receptor Generation Characterize the Acquired Immunodeficiency Syndrome," *Clincial Immun. and Immunopath.*, 37:283 (1985).
Farrar et al., "The Lymphokine Cascade: A Systemic Model of Immunoregulation, Regulation of the Immune Response," 8th Int. Convov. Immunol., Amerherst, NY, 1982, pp. 76–87 (1983).

(List continued on next page.)

*Primary Examiner*—David Saunders
*Attorney, Agent, or Firm*—Rockey, Milnamow & Katz, Ltd.

[57] ABSTRACT

The ability of mononuclear leukocytes to respond to standard stimuli is measured based on the expression of activation antigens on mononuclear cell subclasses. In a preferred embodiment, a sample of mononuclear leukocytes is cultured for up to 24 hours with a standard stimulus known to activate such cells. After culturing, aliquots of the cells are incubated with fluorophore-conjugated monoclonal antibodies to antigenic determinants of a particular mononuclear subclass and different fluorophore-conjugated monoclonal antibodies to particular activation antigens. The incubated aliquots are analyzed on a flow cytofluorometer, whereby each cell is illuminated with a particular light (e.g. argon ion laser), which detects and measures forward light scatter, orthogonal light scatter and two different wavelengths of light emitted from the fluorophores. These parameters are used to identify and enumerate the cells of different subclasses present within the mononuclear leukocyte sample, the cells of said subclasses which have been induced to express a particular activation antigen and the quantity of the activation antigen on said cells. An analysis of these enumerations is shown to correlate with the immunoregulatory status of the mononuclear leukocyte immune system. Data generation and analysis can be performed using a flow cytofluorometric apparatus with data and control signal processing to ensure accuracy and reproducibility of the results of the assay.

17 Claims, 8 Drawing Sheets

OTHER PUBLICATIONS

Filipovich et al., "The Correlation Between Inducer/Suppressor Ratios, Generation of Concanavalin A–Activated Suppressor Cells, and Mitogen–Stimulated Proliferation of Peripheral Blood Lymphocytes in Patients with Alopecia Areata and Normal Controls," *Clin. Immuno. and Immunopath.*, 25:21 (1982).

Fox et al. I, "TA$_1$, A Novel 105 KD Human T Cell Activation Antigen Defined by a Monoclonal Antibody," *J. Immuno.*, 133:1250 (1984).

Fox et al. II, "Activation of Human Thymocytes via the 50kd T11 Sheep Erythrocyte Binding Protein Induces the Expression of Interleukin 2 Receptors on Both T3+ and T3– Populations," *J. Immuno.*, 134:330 (Jan., 1985).

Gillis et al., "Glucocorticoid–Induced Inhibition of T–Cell Growth Factor Production. 1. The Effect on Mitogen–Induced Lymphocyte Proliferation," *J. Immuno.*, 123:1624 (1979).

Harris et al., "The Measurement of Leukoycyte Subsets in the Peripheral Blood of Cancer Patients with Solid Tumors Using Monoclonal Antibody Reagents," *Medical and Pediatric Oncology*, 10:185 (1982).

Haynes et al., "Immune Responses of Human Leukocytes In Vitro," *Progress in Clinical Immunology*, vol. 4, Chapter 10 (1980).

Hercend et al., "Comparative Expression of T9, T10 and Ia Antigens on Activated Human T–Cell Subsets," *Human Immuno.*, 3:247 (1981).

Herman et al., "Expression of Interleukin–2 Receptors and Binding of Interleukin–2 by Gamma Interferon–Induced Human Leukemic and Normal Monocytic Cells," *J. Ex. Med.*, 162:1111 (Sep., 1985).

Hoffman et al., "Simple and Rapid Measurement of Human T Lymphocytes and Their Subclasses in Peripheral Blood," *Proc. Nat. Acad. Sci.*, (No. 8) 77:4914 (1980).

Kristensen et al., "Human Lymphocyte Proliferation 1. Correlation Between Activated and Proliferating T–Lymphocytes," *Immunology Letters*, 5:59 (1982).

Landay et al., "Characterization of a Phenotypically Distinct Subpopulation of LEU–2+ Cells That Suppresses T Cell Proliferative Responses," *J. Immuno.*, 131:2757 (1983).

Lanier et al. I, "Correlation of Functional Properties of Human Lymphoid Cell Subsets and Surface Marker Phenotypes Using Muliparameter Analysis and Flow Cytometry," *Immuno. Rev.* 74:143 (1983).

Lanier et al. II, "Subpopulations of Human Naturtal Killer Cells Defined by Expression of the Leu–7 (HNK–1) and Leu–11 (NK–15) Antigens," *J. Immuno.*, 131:1789 (1983).

Lanier et al. III, "Human Lymphocyte Subpopulations Identified by Using Three–Color Immunofluorescence and Flow Cytometry Analysis," *J. Immuno.*, 132:151 (1984).

Lazarovits et al., "Lymphocyte Activation Antigens I. A Monoclonal Antibody Anti–Act I, Defines a New Late Lymphocyte Activation Antigen," *J. Immuno.*, 133:1857 (1984).

Lipkowitz et al, "Expression of Receptors for Interleukin 2: Role in the Commitment of T Lymphocytes to Proliferate," *J. Immuno.*, 132:31 (1984).

Loken et al., "Two–Color Immunofluorescence Using a Fluorescence–Activated Cell Sorter," *J. Histochem. & Cytochem.*, 25:899 (1977).

Louie et al., "Immunodeficiency and Pathogenesis of Non–Hodgkin's Lymphoma," Seminars in Oncology (No. 3) 7:267 (1980).

Lovett et al., "Application of Flow Cytometry to Diagnostic Pathology," *Lab. Invest.*, 50:115 (1984).

Marti et al., "Normal Human Blood Density Gradient Lymphocyte Subset Analysis: 1. An Interlaboratory Flow Cytometric Comparison of 85 Normal Adults," *Amer. J. Hemato.*, 20:41 (1985).

Martin, "A 44 Kilodalton Cell Surface Homodimer Regulates Interleukin 2 Production by Activated Human T Lymphocytes," *J. Immuno.*, 136:3282 (May, 1986).

Mayawaki et al., "Cyclosporin A Does Not Prevent Expression of Tac Antigen, A Probably TCGF Receptor Molecule, On Mitogen–Stimulated Human T Cells," *J. Immuno.*, 130:2737 (1983).

Merrill et al., "Response to and Production of Interleukin 2 by Peripheral Blood and Cerebrospinal Fluid Lymphocytes of Patients with Multiple Sclerosis," *J. Immuno.*, 133:1931 (1984).

Meuer et al. I, "Cellular Origin of Interleukin 2 (IL 2) in Man: Evidence for Stimulus–Restricted IL–2 Production by T4+ and T8+ T Lymphocytes," *J. Immuno.*, 129:1076 (1982).

Meuer et al., II, "An Alternative Pathway of T–Cell Activation: A Functional Role for the 50 kd T11 Sheep Erythrocyte Receptor Protein," *Cell*, 36:897 (1984).

Miyasaka et al., "Interleukin 2 Deficiencies In Rheumatiod Arthritis and Systemic Lupus Erythematosus," *Clinical Immuno. And Immunopath.*, 31:109 (1984).

Mizel, "Interleukin 1 and T Cell Activation," *Immuno. Rev.*, 63:51 (1982).

Oi et al., "Fluorescent Phycobiliprotein Conjugates for Analyses of Cells and Molecules," *J. Cell Bio.*, 93:891 (1982).

Penn et al., "Depressed Immunity and the Development of Cancer," *Clin. Exp. Immunol.*, 46:459 (1981).

Phillips et al., "Natural Killer Cells Activated in a Human Mixed Lymphocyte Response Culture Identified by Expression of LEU–11 and Class II Histocompatibility Antigens," *J. Exp. Med.*, 159:993 (1984).

Rabinovich et al., "Simultaneous Cell Cycle Analysis and Two–Color Surface Immunofluorescence Using 7–Amino-–Actinomycin D and Single Laser Excitation: Applications to Study of Cell Activation and the Cell Cycle of Murine LY–1 B Cells," *J. Immuno.*, 136:2769 (Apr., 1986).

Reinherz et al., "Abnormalities of Immunoregulatory T Cells In Disorders of Immune Function," *N. Eng. J. Med.*, 301:19 (Nov. 8, 1979).

Salzman et al., "Cell Classification By Laser Light Scattering: Identification and Separation of Unstained Leukocytes," *ACTA Cytologica*, 19:374 (1975).

Scher and Mage, "Cellular Identification and Separation," *Fundamental Immunology*, Chapter 29, 767 (1984), (ed. W.E. Paul).

Smolen et al., "Heterogeneity of Immunoregulatory T–Cell Subsets in Systemic Lupus Erythematosus," *Ameri. J. Med.*, 72:783 (1982).

Uchiyama et al., "A Monoclonal Antibody (anti–TAC) Reactive With Activated and Functionally Mature Human T Cells," *J. Immuno.*, 126:1398 (1981).

Urdal et al., "Purification and Chemical Characterization of the Receptor for Interleukin 2 from Activated Human T Lymphocytes and from a Human T–cell Lymphoma Cell Line," *Proc. Natl. Acad. Sci.*, 81:6481 (1984).

Wakasugi et al., "IL 2 Receptor Induction on Human T Lymphocytes: Role for IL 2 and Monocytes," *J. Immuno.*, 135:321 (Jul., 1985).

Waldman, "The Structure, Function and Expression of Inteleukin–2 Receptors on Normal and Malignant Lymphocytes," *Science*, 232:727 (May, 1986).

Weiss et al., "The Role of T3 Surface Molecules in the Activation of Human T Cells: A Two–Stimulus Requirement for IL–2 Production Reflects Event Occurring at a Pre–Translational Level," *J. Immuno.*, 133:132 (1984).

Welte et al., "Interleukin 2 Regulates the Expression of TAC Antigen on Peripheral Blood T Lymphocytes," *J. Exp. Med.*, 160:1390 (1984).

Williams et al., "The Events of Primary T Cell Activation Can Be Staged By Use of Sepharose–Bound Anti–T3 (64.1) Monoclonal Antibody and Purified Interleukin–1," *J. Immuno.*, 135:2249.

*Monoclonal Antibody Detecting Cell Proliferation and Activation, Anti–Interleukin–2–Receptor*(CD25) (Becton Dickinson) (1985).

Bucy, Ralph P., "Alloantigen–Specific Supppressor T Cells Are Not Inhibited By Cyclosporin A, But Do Require IL 2 For Activation," *J. of Immunology*, 137:809–818 (1986).

Buurman et al., "Cyclosporin A Inhibits IL 2–Driven Proliferation of Human Alloactivated T Cells," *J. of Immunol.*, 136(11):4035–4039 (1986).

Cantrell et al., "The Interleukin–2 T–Cell System: A New Cell Growth Model," *Science*, 224:1312–1316 (1984).

Dos Reis et al., "Effect Of Cyclosporin A On T Cell Function In Vitro: The Mechanism Of Suppression Of T Cell Proliferation Depends On The Nature of The T Cell Stimulus As Well As The Differentiation State of The Responding T Cell," *J. of Immunol.*, 129(6):2360–2367 (1982).

Gillis et al., "Glucocorticoid–Induced Inhibition of T Cell Growth Factor Production. I. The Effect on Mitogen–Induced Lymphocyte Proliferation," *J. Of Immunol.*, 123(4):1632–1638 (1979).

Hess et al., "Effect of Cyclosporin A In Human Lymphocyte Responses In Vitro. III. CsA Inhibits the Production of T Lymphocyte Growth Factors in Secondary Mixed Lymphoecyte Respones But Does Not Inhibitathe The Response Of Primed Lymphocyte To TCGF," *J. of Immunol.*, 128:355–359 (1982).

Hess et al., "Effect of Cyclosporin A In Human Lymphocyte Responses In Vitro. V. Analysis of Responding T Lymphocyte Subpopulations In Primary MLR with Monoclonal Antbodies," *J. of Immuol.*, 717–721 (1983).

Kupiec–Weglinski et al., "Therapy With Monoclonal Antibody To Interleukin 2 Receptor Spares Suppressor T Cells And Prevents or Reverses Acute Allograft Rejection In Rats," *Proc. Natl. Acad. Sci. USA*, 83:2624–2627 (1986).

Lillehoj et al., "Differential Effect of Cyclosporin A On The Expression T and B Lymphocyte Activation Antigens," *J. of Immunol.*, 133:244–250 (1984).

Reed et al., "Effect of Cyclospori A and Dexamethasone On Interleukin 2 Receptor Gene Expression," *J. of Immunol.*, 137:150–154 (1986).

Reem et al., "Interleukin 2 Regulates Expression of Its Receptor and Synthesis of Gamma Interferon by Human T Lymphocytes," *Science*,225:429–430 (1984).

Smith et al., "Interleukin 2 Regulates Its Own Receptors," *Proc. Natl. Acad. Sci. USA*, 82:864–868 (1985).

LYMPHS % IN INTERVAL = 64.19
INTEGRAL = 10132

LEVELS = 1  4  15
LGF 22 63
LRF 25 63

LEVELS = 1  4  15
LGF 17 63
LRF 25 63

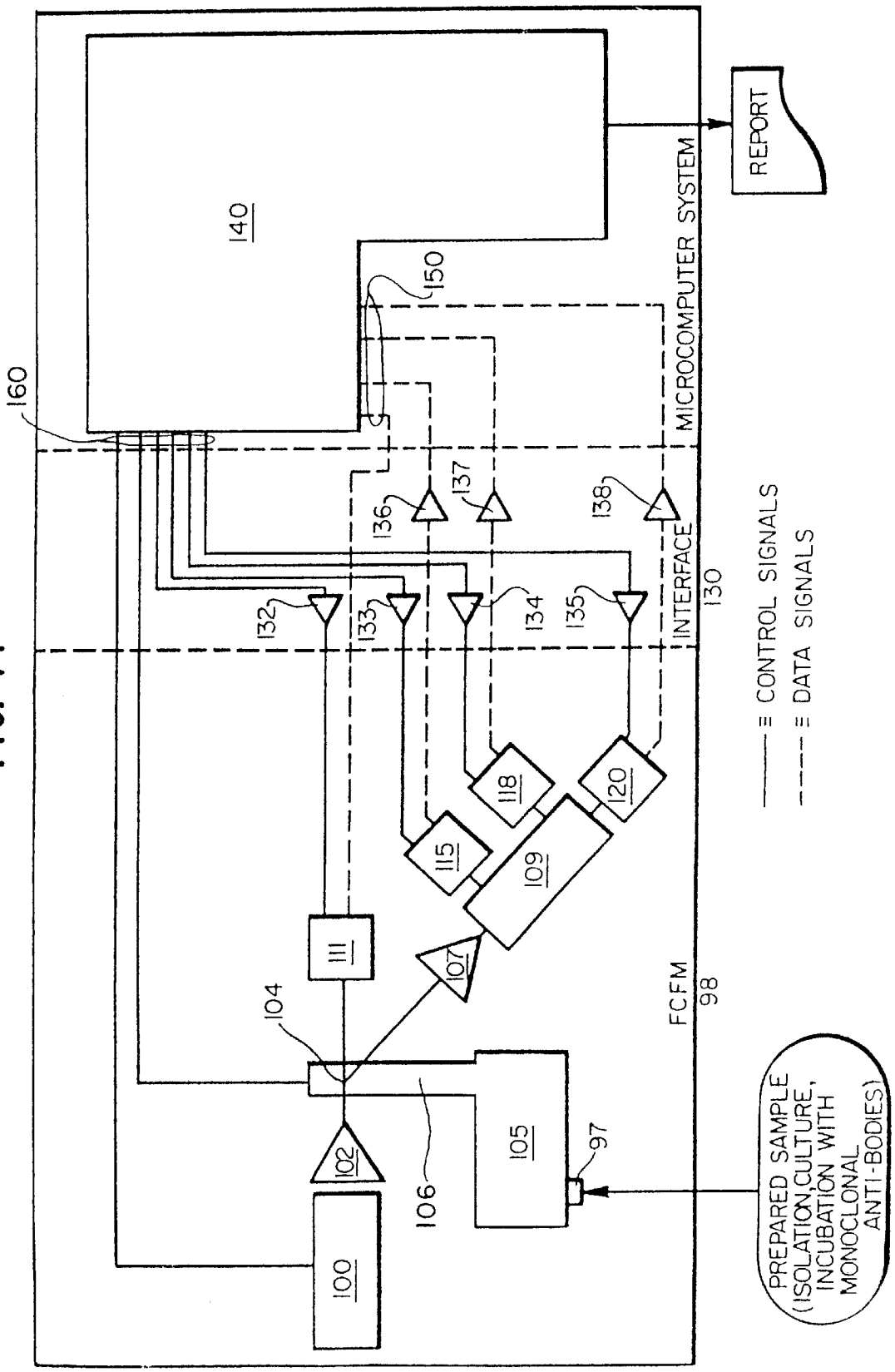

METHOD FOR THE ASSESMENT OF THE MONONUCLEAR LEUKOCYTE IMMUNE SYSTEM

This application is a continuation of U.S. Ser. No. 08/406,381filed Mar. 17, 1995, U.S. Pat. No. 5,656,446, which is a continuation of U.S. Ser. No. 08/144,481, filed Sep. 9, 1993, U.S. Pat. No. 5,445,939, which is a continuation of U.S. Ser. No. 07/751,620, filed Oct. 28, 1991, now abandoned, which is a continuation of U.S. Ser. No. 07/415,905, filed Oct. 2, 1989, now abandoned, which is a continuation of U.S. Ser. No. 06/895,754, filed Aug. 12, 1986, now abandoned.

FIELD OF THE INVENTION

This invention relates to an apparatus and automated method to perform an analysis of the mononuclear leukocyte immune system's ability to respond to standard stimuli. Data concerning activation antigen expression on particular subclasses of stimulated mononuclear cells that have interacted over time is collected using flow cytofluorometric techniques. An analysis of activation antigen expression on these stimulated mononuclear cell subclasses correlates with the immunoregulatory status of the mononuclear leukocyte immune system.

This assay provides an analysis of the interaction of mononuclear cells in vitro, such interaction dependent upon the immunoregulatory status of the individual from whom the sample of cells was obtained. Therefore, the results of this assay can be used as a measure of the immunoregulatory status of the in vivo mononuclear leukocyte immune system. Analysis of this data can explain the heterogeneity of mitogen response among normals, better define immunoregulatory abnormalities in a variety of immune-mediated disorders, and provide a method for monitoring in vivo immunomodulation therapy involving suppression or potentiation of mononuclear cell activation. The assay also involves the use of a flow cytofluorometric apparatus having certain modifications, in terms of data and control signal processing, which allows for more accurate and reproducible measurements of the stimulated mononuclear cells.

BACKGROUND AND PRIOR ART

The immune system is a regulatory system that maintains homeostasis by protecting the body against foreign particles, such as pathogenic microbial agents, and against native cells that have undergone neoplastic transformation. The immune system exerts its control within the body by virtue of circulating components, humoral and cellular, capable of acting at sites removed from their point of origin. The complexity of the immune system is derived from an intricate communications network capable of exerting multiple effects based on relatively distinct cell types.

The cellular component of the immune system consists of relatively distinct cell types. Using morphologic criteria the cellular component can be divided into classes; e.g. granulocytes, lymphocytes and monocytes. The morphologic criteria include differences in cell size and intracellular organelles such as the nucleus. Of these classes, lymphocytes, monocytes and related cells are grouped together as mononuclear cells.

Further distinction of cell types involves dividing the cells into subclasses using certain cell surface structures termed antigenic determinants; that is, within a class of cells there exist particular antigenic determinants which define relatively distinct cell types, i.e., subclasses. It should be noted that other antigenic determinants or combinations of antigenic determinants can be used to further delineate subclasses; the term class, hereinafter, refers to distinction of cell types based on morphologic criteria, while subclass refers to the distinction based on criteria relating to morphology and expression of antigenic determinants.

The major mononuclear cell classes of the immune system are monocytes and lymphocytes. There exists other classes of mononuclear cells; e.g. lymphoblasts and large granular lymphocytes thought to be natural killer cells. Peripheral blood monocytes are derived from bone marrow monocytes. Human lymphocytes are derived from two areas, the thymus and the "bursa"-equivalent. These areas are referred to as the central lymphoid system. The peripheral lymphoid system consists of mature lymphocytes which can be found in lymphatics, spleen, lymph nodes, lymphoid tissue of the GI tract, respiratory tracts, sectory glands and blood. Mononuclear leukocytes found at these "peripheral" locations are hereinafter referred to as peripheral mononuclear cells. Mature mononuclear leukocytes are referred to as immunocompetent cells and taken together constitute the mononuclear leukocyte immune system.

Mononuclear leukocytes can be divided into subclasses. For example, there are two major types of lymphocytes; T lymphocytes, which are referred to as T-cells and B lymphocytes which are referred to as B-cells. T-cells constitute a group of related subclasses which participate in a variety of cell-mediated immune reactions. These subclasses can be distinguished in a sample of leukocytes by their morphology which identifies them as lymphocytes and the particular antigenic determinants which delineate the subclass. T-cell subclasses are involved in different cell-mediate regulatory functions, such as enhancement or suppression of an immune response, and are directly involved in effector functions, such as the cytotoxic destruction of viral infected, foreign or malignant cells.

Mononuclear cells communicate, i.e. interact, by direct cell—cell contact or via soluble factors. These soluble factors are termed lymphokines, if secreted by lymphocytes, or monokines, if secreted by monocytes. Immunocompetent cells can express highly specific receptors for a particular lympho/monokine on their cell surface. Binding of a lympho/monokine with its receptor initiates or facilitates certain intracellular events.

For example, the proliferation of lymphocytes is influenced by certain lymphokines. Interleukin-2 (hereinafter IL-2) is a lymphocyte derived factor that promotes long-term proliferation of T-cell lines in culture. Upon activation, the T-cell produces IL-2 and IL-2 receptors, also referred to as IL2R. The binding of IL-2 to IL-2 receptors triggers T-cells to proceed from the $G_o/G_I$ into the S phase of the cell cycle (D. A. Cantrell and K. A. Smith, "Transient Expression of Interleukin-2 Receptors: Consequences for T-Cell Growth," *Journal Of Experimental Medicine*, (158) 1895–1911 (1983)) and regulates the production of other lymphokines. The failure of production of either IL-2 or its receptor, results in failure of many T-cell immune responses. IL-2 receptors have also been found on B-cells and monocytes. IL-2 also upregulates the expression of IL-2 receptors, i.e. it increases the amount of IL-2 receptors expressed on the cell surface. K. Welte, et al., "Interleukin 2 Regulates The Expression of TAC Antigen on Peripheral Blood T Lymphocytes," *Journal of Experimental Medicine*, (160) 1390–1403 (1984). An example of an important monokine is interleukin-1 (hereinafter IL-1) which appears to be essential for the amplification of many T-cell dependent immune responses. IL-1 induces the expression of certain E-rosette receptors and stimulates the production of the lymphokine, IL-2. S. B. Mizel, "Interleukin-1 and T-cell Activation," *Immunologic Review*, (63) 51–72 (1982). It is believed that a particular 44 kilodalton protein, found on 80% of mature T-cells, might function as the receptor for the monokine, IL-1.

The induction of the mononuclear leukocyte immune system response to a foreign (e.g. virus or organ transplant) or altered (e.g. neoplastic) antigen involves the activation of the mononuclear cells, such as lymphocytes, with receptors for the particular antigen. This activation entails a sequence of events initiated when the antigen binds to the receptor. Activation provides for cell differentiation and proliferation into a clone of cells to respond to the antigen.

Activation is not necessarily a linear sequence of events, often events occur simultaneously, and not all events lead directly to cell division. Important activation events include: cross-linking of certain cell surface molecules, certain intracellular events leading to activation of certain enzymes, such enzymes facilitating increased protein synthesis including production of certain lympho/monokines and activation antigens, expression of activation antigens including certain lympho/monokine receptors on the cell surface, the regulation of these events by enhancing or suppressing regulatory signals (e.g. certain lympho/monokines), replication of DNA and cell division. The increase in protein synthesis can occur as early as one hour, with DNA replication beginning about 36 hours, after the initial stimulus. These activation events are not necessarily uniform for each mononuclear cell subclass and the response to the regulatory signals is not uniform; therefore, the activation of the cells of the mononuclear leukocyte immune system is asynchronous in nature due to their heterogeneity. R. F. Ashman, "Lymphocyte Activation", *Fundamental Immunology*, 267–300 (1984).

A stimulus can initiate mononuclear cell activation by cross-linking certain cell surface molecules. An antigen achieves such cross-linking when it is rendered functionally multivalent after interaction with antigen-presenting cells, often monocytes. Certain multivalent glycoproteins, termed lectins, obtained from plant or animal sources can cross-link certain surface molecules thereby activating lymphocytes, some even induce division of cells. Substances which initiate activation leading to division of cells are termed mitogens. Examples of lectins, which act as mitogens, include phytohemagglutinin (hereinafter PHA), concanavalin A and pokeweed mitogen.

On lymphocytes, both the T-cell antigen receptor and the E-rosette receptor surface molecules can be crosslinked thereby activating cells. For example, the monoclonal antibody OKT3 which identifies and binds to the T-cell antigen receptor can act as a mitogen. The mitogenic effects of the lectin phytohemagglutinin are mediated via the E-rosette receptor. Therefore, stimuli which initiate activation of the mononuclear leukocyte immune system can include antigens, antibodies and certain lectins. Multivalency, which is important for cross-linking, is either an inherent property of the activating substance, achieved biologically by interaction with antigen-presenting cells or achieved artificially by binding to a substrate, e.g. Sepharose beads.

After a stimulus has initiated a sequence of activation events, there is an increased expression of certain cell surface proteins not easily detected on resting cells. These are referred to as activation antigens. Activation antigens include receptors for certain lympho/monokines. One such activation antigen is the IL-2 receptor, which is also referred to as the TAC antigen, and has been shown to be detectable within 6 hours and reaches maximal expression 72 hours after initiation of activation. D. A. Cantrell and K. A. Smith, ibid.

Other activation antigens expressed on the cell membrane include DR, the transferrin receptor, an epitope of the E-rosette receptor termed $T11_3$, T10, $Ta_1$, Ba, 4F2, A1–3 and Act I. See, e.g., A. I. Lazaroutis, et al., "Lymphocyte Activation Antigens: I. Monoclonal Antibody, Anti-Act I, Defines a New Late Lymphocyte Activation Antigen," *Journal of Immunology*, (133) 1857–62 (1984). Particular activation antigens are not necessarily unique to one class or subclass of mononuclear cells and they are not each expressed at the same time during the sequence of activation events. Therefore, at a certain length of time after a stimulus has initiated mononuclear cell activation, the degree to which a certain activation antigen is expressed will depend on the particular sequence of preceding events and the regulatory influences on the mononuclear cell which expresses it.

The function of all the activation antigens is not yet known. The transferrin receptor binds transferrin which has been shown to enhance response of mononuclear cells to mitogens and might be involved in natural killer cell differentiation. The expression of receptors for certain lympho/monokines, e.g. IL-2 receptor, is important in the propagation of activation events after initiation by a stimulus.

The response of the mononuclear leukocyte immune system to foreign or altered antigens, thus involves a complicated regulatory network consisting of different subclasses of cells with distinct functions interacting by direct contact and/or lympho/monokines. Damle, et al., "Immunoregulatory T Cell Circuits in Man," *Journal of Immunology*, (134) 235–43 (1985). A particular stimulus will initiate a sequence of activation events in individual cells of certain mononuclear cell subclasses. The sequence is not necessarily linear, nor do all cells begin or spend an equal amount of time at each step of the sequence. The sequence of activation events includes expression of receptors for and production of certain lympho/monokines each with particular regulatory functions with regards to mononuclear cell differentiation and proliferation. J. J. Farrar and W. R. Benjamin, "The Lymphokine Cascade: a Systemic Model of Immunoregulation," *Regulation of the Immune Response*. 8th Int. Convoc. Immunol., 76–87 (1982).

Variations in the sequence of activation events are determined by the subclass to which the cell belongs and the effects of these regulatory signals. This activation of individual cells of the mononuclear leukocyte immune system in the presence of the system's regulatory communications network results in differentiation and clonal proliferation of regulatory and effector subclasses, neutralization of the inciting factor(s) and eventual return of the system to a steady state, which can be more or less quiescent. This state determines the mononuclear leukocyte immune system's ability to respond to a stimulus appropriately with regards to the length of time to initiate, the nature and the intensity of the response. This "initial" state of the mononuclear leukocyte immune system can be termed the immunoregulatory status.

Over the past 10 years, new methodologies have been developed to analyze the complex regulatory and effector functions of the mononuclear leukocyte immune system. The development of monoclonal antibodies has facilitated the identification and enumeration of the different subclasses in the mononuclear leukocyte immune system. These antibodies can bind to cell surface structures, e.g. antigenic determinants. The binding of a monoclonal antibody to a cell can be determined using a fluorescent microscope, if the antibody has been directly or indirectly conjugated to a fluorophore. Monoclonal antibodies to the T-cell antigen receptor, e.g. anti-OKT3, anti-CCT3 and anti-Leu-4, are used to identify and enumerate T-cells. Monoclonal antibodies can be used to identify and enumerate other mononuclear cell subclasses, for example: helper/inducer T lymphocytes, e.g. anti-OKT4, anti-CCT4 and anti-Leu-3a; suppressor/cytotoxic T lymphocytes, e.g. anti-OKT5, anti-OKT8, anti-CCT8 and anti-Leu-2a; natural killer cells, e.g. anti-Leu-11 ; B-cells, e.g. anti-Leu-12; monocytes, e.g. anti-Leu-M3. Kung in U.S. Pat. No. 4,364,932 and in U.S. Pat. No. 4,381,932 and in U.S. Pat. No. 4,381,245; G. E. Manti, et al., "Normal Human Blood Density Gradient Lymphocyte Subset Analysis: I. An Interlaboratory Flow Cytometric Comparison of 85 Normal Adults," *American Journal of Hematology* (2) 41–52 (1985); etc.

Antibodies binding to the same or similar antigenic determinants are used to group these determinants into "Clusters of Differentiation." A. Bernard, et al., "The Clusters of Differentiation (CD) Defined by the First International Workshop on Human Leucocyte Differentiation Antigens," *Human Immunology*, (11) 1–10 (1984). It should be noted that the antigenic determinants identified by monoclonal antibodies can be found on cells from different classes of mononuclear leukocytes, e.g. Leu-3a is found on monocytes and lymphocytes. As stated previously, subclass distinction relies on both morphologic and antigenic determinant criteria. Also, the amount of antigenic determinant expressed on the cell surface and identified by monoclonal antibodies can change with activation of the cell, e.g. the amount of Leu-4 appears to decrease after initiation of the activation.

Further subclass delineation often requires identifying two distinct antigenic determinants on the same cell. For example, the inducer of suppression subclass can be identified and enumerated using anti-Leu-3a and anti-Leu-8 or anti-2H4, the helper subclass can be identified and enumerated using anti-Leu-3a and anti-4B4, and the suppressor subclass can be identified and enumerated using anti-Leu-2a and anti-Leu-15. N. K. Damle, ibid., etc.

Monoclonal antibodies have also been developed which bind to the activation antigens, e.g. anti-OKT9 (transferrin receptor) and anti-Interleukin-2 Receptor (hereinafter anti-IL2R). T. Uchiyama, et al., "A Monoclonal Antibody (Anti-Tac) Reactive with Activated and Functionally Mature Human T-Cells," *Journal of Immunology* (126) 1393–1403 (1981); D. L. Urdal, et al., "Purification and Chemical Characterization of the Receptor for Interleukin-2 from Activated T Lymphocytes and from a Human T-cell Lymphoma Cell Line", *Proc. Natl. Acad. Sci.*, (81) 6481–85 (1984).

Flow cytofluorometric techniques have been developed to differentiate mononuclear cell subclasses, such as helper/inducer and suppressor/cytotoxic T-cells, using monoclonal antibodies and an apparatus to determine morphologic characteristics and to detect different antigenic determinants. Hansen in U.S. Pat. No. 4,284,412 discusses a method and apparatus for automated identification and enumeration of specified blood cell lymphocyte subclasses. In Hansen's assay, a sample of whole blood or buffy coat is incubated with a monoclonal antibody which is selectively reactive with a distinct antigenic determinant identifying a subclass of lymphocytes. Antibodies which bind to a particular antigenic determinant are conjugated to a fluorophore (also referred to as a fluorochrome or fluorescer), directly or indirectly, such that they will be fluorescently responsive to particular light (e.g. argon ion laser). Single cells are identified and differentiated based on the measurement of two light scatter parameters and the amount of fluorescence. Ranges of values are set using electronics for the two light scatter parameters such that "an area of interest", also referred to as a "window", is formed discriminating the lymphocytes. For each cell in the area of interest, the amount of fluorescence is used to determine if the cell has the antigenic determinant expression typical of the subclass.

It should be noted that in addition to whole blood or buffy coat, appropriate samples for incubation can be obtained from the interface after density gradient centrifugation of whole blood. Marti, et al., ibid. This interface yields mostly mononuclear cells, although it can contain immature granulocytes. Also, the samples of incubated cells can be fixed with 1% paraformaldehyde and stored at 4° C. for approximately seven days until performing flow cytofluorometric measurements.

A flow cytofluorometer is an instrument capable of measuring properties of single cells as they pass through an orifice at high velocity. I. Scher & M. Mage, "Cellular Identification and Separation," *Fundamentals Immunology*, 767–68 (1984). The measurements made using a flow cytofluorometer are performed on cells suspended in a a stream of fluid that is intersected by a beam of light, e.g. coherent light from an argon ion laser. Lasers are particularly important in these systems since they provide a source of intense, highly collimated (parallel light waves) and monochromatic light, which can be focused to deliver a large amount of energy to the cells being analyzed. When a cell in the fluid stream intersects the beam, the light is scattered. Low angle forward (approximately 2–15 degrees to the angle of incident light) and orthogonal (approximately 90 degrees to the intersection of the incident light and stream) scattered light can be detected and measured. It should be noted that light scatter at other angles can also be detected and measured. The low angle forward (hereinafter forward) light scatter detector is located directly in line with the laser beam. The orthogonal light scatter and fluorescent collection lens is placed orthogonal to the intersection of the laser beam and stream. Measurement of orthogonal light scatter utilizes a photomultiplier tube (hereinafter PMT). The light accepted by the forward light scatter detector and orthogonal collection lens is approximately a cone of half angle 20°.

The measurements of forward and orthogonal light scatter have been found to relate to cell size and intracellular structures, respectively. It should be noted that certain flow cytofluorometers use a measurement of cell volume, instead of forward light scatter, as one of two parameters to delineate leukocyte classes. Red blood cells, platelets and debris yield the lowest levels of forward and orthogonal light scatter. Threshold triggers on the flow cytofluorometer can be set so that light scatter data will not be generated by these. Dead cells will yield lower forward and orthogonal light scatter measurements than their live counterparts. Due to differences in size and intracellular structures, different leukocyte classes can be differentiated using the forward and orthogonal light scatter parameters. Hansen, ibid.; R. A. Hoffman, et al., "Simple and Rapid Measurement of Human T Lymphocytes and Their Subclasses in Peripheral Blood," *Proc. Nat'l. Acad. Sci.*, (77) 1914–17 (1980); Hoffman in U.S. Pat. No. 4,492,752. Most lymphocytes will yield a low level of both forward and orthogonal light scatter. Most monocytes will yield a higher level of forward and slightly higher level of orthogonal light scatter. It should be noted that most granulocytes will yield a level of forward light scatter overlapping that of lymphocytes and monocytes, however, the orthogonal light scatter will be much higher than either of these classes. Light scatter "areas of interest" can be demarcated such that each of these classes can be identified. There are important mononuclear cell classes which overlap these divisions based on forward and orthogonal light scatter parameters. These include lymphoblasts and natural killer cells, which can yield light scatter parameters similar to monocytes. In such cases fluorophore-conjugated monoclonal antibodies can be used to facilitate the delineation of subclasses of these mononuclear cell classes.

The laser is often tuned so that light of 488 nanometers (hereinafter nm) is produced. This wavelength of light provides an optimal excitation for fluorescein-isothiocyanate (hereinafter FITC). FITC is commonly used as a fluorophore which-is conjugated to monoclonal antibody probes. When the cell being analyzed has bound fluorophore-conjugated monoclonal antibody, light is emitted from the excitation of the fluorophore by the laser light, e.g. FITC emits light in the green spectrum (hereinafter green fluorescence). The light-emitted enters a collection lens and then passes through a series of filters, which allow only a certain wavelength of light to enter a fluorescence detector, usually a PMT. Fluorescence detectors, as well as light scatter detectors, produce an electronic signal as output which can be used by a device to analyze the measured parameter data.

The amount of fluorescence emitted by a cell in the laser beam is proportional to the number of fluorophores excited. A monoclonal antibody can be conjugated to a known number of fluorophores. Therefore, the size of the electronic signal produced by the fluorescent detector is proportional to the number of monoclonal antibodies bound to the cell and thereby is a measure of the number of antigenic determinants (or activation antigens) detected on the cell surface. Therefore, a cell can be assigned to a specific subclass within a class of mononuclear leukocytes using forward light scatter, orthogonal light scatter and fluorescence parameters.

With a flow cytofluorometer configured with three PMTs set along an axis orthogonal to the stream and the light beam axes, two wavelengths of emitted light can be detected in addition to orthogonal light scatter. Filters are used to isolate the wavelength of emitted light to be detected by each PMT. This technique facilitates dual parameter fluorescent measurements of cells which have been incubated with two monoclonal antibodies, each binding to a different antigenic structure on the cell surface, e.g. two different antigenic determinants. The monoclonal antibodies are usually directly conjugated to fluorometrically distinguishable fluorophores which emit different wavelengths of light when illuminated with laser light. Even with the use of filters to isolate specific wavelengths of emitted light for detection, there is usually some overlap of the emission spectra detected by the PMTs. Most flow cytofluorometers have an electronic compensation network which can be set by the operator to correct for the overlap. M. R. Loken, et al., "Two-Color Immunofluorescence Using a Fluorescence-Activated Cell Sorter," *Journal of Histochemistry and Cytochemistry*, (25) 899–907 (1977).

In addition to FITC, Texas Red dye (conjugated to avidin and then incubated with a biotinylated monoclonal antibody) is often used for dual fluorescent measurements. This dye is optimally excited by light at a wavelength of 568 nm thereby requiring a second laser. The light from the second laser is focused onto the stream slightly below the intersect point of the first laser. Such a two laser system requires appropriate signal delay electronics so that light scatter and both fluorescence parameters are assessed simultaneously. A recently discovered fluorescent compound, phycoerythrin (hereinafter PE) (see Stryer in U.S. Pat. No. 4,520,110), can be conjugated to monoclonal antibodies and utilized for dual parameter fluorescent measurements with FITC by a single laser system, as it can also be excited by light at a wavelength of 488 nm. The light emitted by PE is in the orange-red spectrum (hereinafter red fluorescence). V. T. Oi, et al., "Fluorescent Phycobiliprotein Conjugates for Analyses of Cells and Molecules," *Journal of Cell Biology*, (93) 981–86 (1982). The use of dual parameter fluorescent measurements has facilitated further subclass delineation within classes of mononuclear leukocytes and has clarified antigenic determinant expression on subclasses, e.g. high levels of Leu-2a are found on the suppressor/cytotoxic subclass while lower levels of Leu-2a are found on natural killer cells. L. L. Lanier and M. R. Loken, "Human Lymphocyte Subpopulations Identified by Using Three-color Immunofluorescence and Flow Cytometric Analysis," *Journal of Immunology*, (132) 151–156 (1984).

To facilitate analysis, data generated by a flow cytofluorometer is usually displayed as a frequency distribution plot, i.e. histogram, with one or two measured parameters displayed. Each two parameter histogram resembles a topographic map with the contours depicting number of cells. The histogram can display data for each cell analyzed or only for those with parameter data within an area of interest. The amount of antigenic determinants and activation antigens detected per cell has a large range necessitating the use of a logarithmic scale to represent fluorescence parameter data for all the cells on the histogram. This is often accomplished using a logarithmic amplification of the electronic signal produced by the preamplifier in the PMT (this signal is often integrated so as to be proportional to the total fluorescence detected by the PMT). It has been found that many antigenic determinants have a lognormal distribution thereby facilitating analysis. This lognormal distribution is often found even after antigenic determinant modulation due to cell activation. Analysis of histograms representing flow cytofluorometric data has been used to enumerate subclasses of mononuclear cells in an attempt to assess the immunoregulatory status of the mononuclear leukocyte immune system.

An altered immunoregulatory status is suspected to be involved in many human diseases, e.g. viral illnesses, autoimmune disease and malignancy. Autoimmune disease involves a primary defect in the mononuclear leukocyte immune system such that self-antigens can initiate activation of the mononuclear cells. In the case of organ transplantation, suppression of the normal immunoregulatory status with medication is required to avert rejection of the transplanted organ. Immunosuppression, whether secondary to medication or due to a disease state, is suspected to contribute to the development of certain malignancies. I. Penn, "Depressed Immunity and the Development of Cancer," *Clinical and Experimental Immunology*, (46) 459–474 (1981). Disorders of normal human physiologic functions involving the immune system can be referred to as immune-mediated disorders.

Peripheral blood samples have been analyzed using monoclonal antibodies and flow cytofluorometry to determine the percentages of T-cell subclasses in patients with different immune-mediated disorders. M. A. Bach and J. F. Bach, "The Use of Monoclonal Anti-T Cell Antibodies to Study T-Cell Imbalances in Human Diseases," *Clin. Exp. Immunol.*, (45) 449–456 (1981). For example, an increase in the ratio of helper/inducer to suppressor/cytotoxic (hereinafter H:S) T-cells have been found in many patients with autoimmune diseases or multiple sclerosis. Increased numbers of suppressor/cytotoxic T-cells have been found in patients with viral illnesses, giving rise to a decreased H:S ratio. In patients with the acquired immunodeficiency syndrome (hereinafter AIDS), there is also a decrease in the H:S ratio, however this is due to decreases in the number of helper/inducer T-cells. In patients with solid tumors, a decrease in the number of helper/inducer and suppressor/cytotoxic T-cells is found, although the percentages were normal. These abnormalities in T-cell subclasses have not been found consistently in all patients with certain diseases and often the abnormalities do not correlate with the degree of disease activity. For example, the H:S ratio has not been found to correlate with disease activity in patients with systemic lupus erythematosus. J. S. Smolen, et al., "Heterogeneity of Immunoregulatory T-Cell Subsets in Systemic Lupus Erythematosus: Correlation with Clinical Features," *American Journal of Medicine*, (72) 783–790 (1982). Also, patients infected with HTLV III, the virus thought to be the etiology of AIDS, do not necessarily have decreased number of helper/inducer T-cells.

In vitro mononuclear leukocyte assays have been developed in an attempt to measure the ability of the mononuclear leukocyte immune system to function appropriately. Traditional in vitro functional assays use mitogens to induce blasteogenesis. The amount of blasteogenesis is then measured by tritiated thymidine uptake in replicating DNA. This type of assay is performed using a fixed concentration of isolated mononuclear cells, which are cultured in the presence of an optimal concentration of a mitogen and then pulsed with tritiated thymidine. Tritiated thymidine uptake is generally measured after culturing the cells for 72 hours. These assays, however, do not allow for an analysis of the mononuclear cell subclasses which have interacted during the induction of blasteogenesis. B. F. Baynes, et al., "Immune Response of Human Lymphocytes In vitro," *Progress In Clinical Immunology*, (4) 23–62 (1980).

Certain diseases are associated with decreased (e.g. malignancies or AIDS) or increased (e.g. multiple sclerosis) in vitro responses to mitogens used in these assays. Immunosuppressive agents, e.g. glucocorticoids and cyclosporin, have been shown to suppress blastogenesis. Research involving immunosuppressive agents has revealed differential inhibitory effects on certain subclasses of lymphocytes. These traditional mitogen assays, however, do not allow for an analysis of the lymphocyte subclasses which have interacted during the induction of blastogenesis or for measurement of the differential inhibitory or potentiating effects which contribute to an altered immunoregulatory status. F. Kristensen, et al., "Human Lymphocyte Proliferation: I. Correlation between T-lymphocytes," *Immunology Letters*, (5) 59–63 (1982).

Similarly, measuring IL-2 receptor expression on the mononuclear cell classes, e.g. lymphocytes, without subclass distinction also has not proven to be useful in delineating many of the possible etiologies of an altered immunoregulatory status. Activation of T-cells results in the expression of specific cell surface receptors for lymphokines, e.g. IL-2 receptor, and the synthesis of lymphokines, e.g. IL-2. Immunosuppressive agents, e.g. glucocorticoids and cyclosporin, have been found to inhibit protein synthesis and specifically to block production of IL-2 by mononuclear cells stimulated with mitogens. Studies using the monoclonal antibody, anti-TAC, indicate that cyclosporin does not block the expression of IL-2 receptor in such cells. T. Miyawaki, et al., "Cyclosporin A Does Not Prevent Expression of Tac Antigen, a Probable TCGF Receptor Molecule, on Mitogen-Stimulated Human T-Cells," *Journal of Immunology*, (13) 2737–42 (1983). In patients infected with HTLV III, only certain patient groups were found to not express IL-2 receptor after stimulation with mitogens. Patients with SLE have normal expression of IL-2 receptor after stimulation with mitogens, while those with rheumatoid arthritis have decreased expression of IL-2 receptor. N. Miryasaka, et al., "Interleukin 2 Deficiencies and Systemic Arthritis and System Lupus Erythematosus," *Clin. Immuno. Immunopath.*, (31) 109–17 (1984). Cereborspinal fluid lymphocytes from MS patients have normal proportions of IL-2 receptor bearing cells, although they had deficient production of IL-2.

SUMMARY OF THE PRESENT INVENTION

The present invention relates to a method and apparatus to assess the immunoregulatory status of the mononuclear leukocyte immune system. The assay described herein distinguishes the altered immunoregulatory status of patients with immune-mediated disorders or receiving immunomodulation therapy from the immunoregulatory status of normal individuals. The method involves culturing mononuclear cells with a standard stimulus and measuring the quantity of activated cells in particular mononuclear cell subclasses. An analysis of these measurements is used to determine the degree of cellular activation in the mononuclear cell subclasses, i.e. the ability of the mononuclear leukocyte immune system to respond to stimuli. The degree of cellular activation is used to assess the in vivo immunoregulatory status of the mononuclear leukocyte immune system.

The assay affords a timely (less than about 24 hours), reproducible and accurate assessment of the immunoregulatory status. These attributes are necessary for a clinical assay to assist the diagnostic and therapeutic decision process, e.g. monitoring for transplanted organ rejection where delay of adequate immunosuppressive therapy could result in loss of an organ.

In particular, this invention relates to a method whereby a sample consisting substantially of peripheral mononuclear cells is cultured with a standard stimulus for a period of time sufficient to initiate a sequence of activation events and allow for measurable cellular activation, as influenced by subclass interaction, to develop. The assay does not involve isolation of specific subclasses prior to stimulation, and therefore preserves and measures the enhancing and suppressing effects of other subclass components of the system as they are present in vivo. Standard stimulus, for the purposes of this assay, is defined as a stimulus consisting of a substance(s) at a known concentration(s) such that a reproducible measure of particular activation antigen expression on select subclass(es) can be obtained on repeat determinations from a sample of mononuclear cells from a normal individual, each after the same length of time in culture with the stimulus. Examples of standard stimuli include, but are not limited to: mitogenic lectins, Sepharose-bound anti-OKT3 with IL-1 and Sepharose-bound specific antigen with IL-1 and IL-2.

Measurement of the amount of cell surface activation antigen expression on select subclasses is performed using fluorometrically distinguishable fluorophore-conjugated monoclonal antibodies and a flow cytofluorometer to collect light scatter and fluorescence parameter data for each cell. The light scatter data is used to identify a particular leukocyte class, while fluorescence data is analyzed to enumerate the cell subclass and the amount of activation antigen expression. The quantity of activated cells in particular subclasses can be determined using a preset minimal amount or a preset range of activation. The degree of cellular activation in select mononuclear cell subclasses is determined from the analyses of this flow cytofluorometric data and used to assess the immunoregulatory status. Generation and analysis of data concerning leukocyte class, cell subclass and the amount of activation antigen expression is performed using a flow cytofluorometric apparatus including a computer device with appropriate software programming. This system contains data and control signal processing to ensure the accuracy and reproducibility of the measurements made and therefore the results produced by the apparatus.

In particular, the present invention can be used to determine the ability of T lymphocyte subclasses to respond to standard stimuli in vitro, while preserving their ability to interact, as they do in vivo. The assay can enumerate certain T-cell subclasses by detecting cells bearing certain antigenic determinants on their cell membrane, e.g. Leu-3a or Leu-2a. After culturing lymphocytes for 18 hours with the standard stimulus, PHA, these T-cell subclasses express a measurable amount of the activation antigen, IL-2 receptor. An analysis to determine the degree of activation of these T-cell subclasses gives a clinical measure of the immunoregulatory status of the individual. In a similar fashion, the assay can determine the degree of activation of other mononuclear cell subclasses, thereby refining this clinical measure.

Using these techniques and procedures, the present invention provides a method and apparatus which is sufficiently sensitive and specific to assess the in vivo kinetics of altered self-regulation of, and effects of immunomodulation therapy on, the mononuclear leukocyte immune system.

BRIEF DESCRIPTION OF THE DRAWINGS

The histrograms shown in these figures were generated from the four parameter data measured by an EPICS V flow cytofluorometer using the MDADS software package (Coulter Corporation, Hialeah, Fla.). Each two parameter histogram has the x and y axes labeled for the parameters they represent. Each axis is divided into 64 equally spaced divisions referred to as channels. The forward light scatter (FLS) axis is linear. The orthogonal (LI90), green fluorescence (LGF) and red flurescence (LRF) axes are logarithmic. The Z axis relates to the number of cells and is linear. In these two dimensional plots, contours are used to indicate Z-axis values and are represented by a scatter density plot. Below each two parameter histogram are the three levels at which contours are drawn. For each one parameter histogram, the y-axis relates to the number of cells. The scale factor for the y-axis is in the upper left-hand corner. The total number of cells represented in the histogram is in the upper right-hand corner.

In some of the figures, areas of interest are demarcated with geometric shapes or cursor lines. The x and y coordinates of the points used to generate the geometric shapes are to the left of the histogram. When used, there are four cursor lines for each two parameter histogram and two for each one parameter histogram. The channel numbers at which the cursor lines are drawn is indicated below each histogram. For two parameter histograms, the axis label (e.g. LGF) is followed by two numbers, each indicating a channel at which a cursor line is drawn. For one parameter histograms, the word "CHANNEL" is followed by two numbers indicating where the two cursor lines are drawn. Also, the number of cells with data parameters which would place them within the specified geometric shape or between the cursor lines as drawn is indicated after the word "INTEGAL". This is expressed as a percent of the total cells represented in the histogram after the words "% IN INTERVAL".

FIG. 14 shows a schematic diagram of a preferred embodiment for the apparatus including flow cytofluorometric and signal processing hardware, a microcomputer system and software to facilitate clinical assessment of the immunoregulatory status of the mononuclear leukocyte immune system.

DETAILED DESCRIPTION

Figure 1:
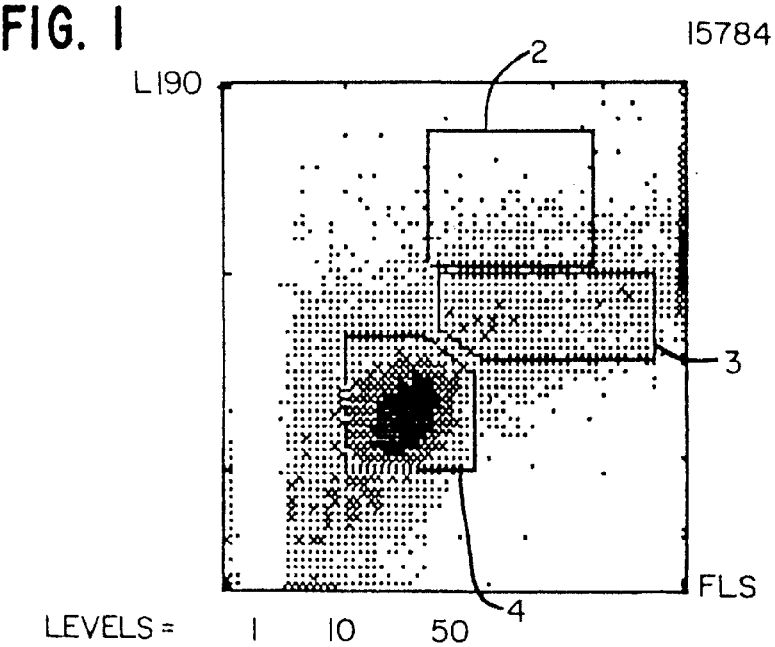
FIG. 1 shows a histogram of forward light scatter and orthogonal light scatter data as measured by a flow cytofluorometer of leukocytes isolated by density gradient centrifugation of peripheral blood with areas of interest demarcated by solid lines.

While this invention is satisfied by embodiments in many different forms, there is shown in the drawings and will herein be described in detail a preferred embodiment of the invention, with this understanding that the present disclosure is to be considered exemplary of the principles of the invention and is not intended to limit the invention to the embodiment illustrated. The examples which follow this detailed description are offered by way of further illustration and not by way of limitation. The scope of the invention will be measured by the appended claims and their equivalents.

In the present assay, a sample containing substantially peripheral mononuclear leukocytes is isolated and the leukocytes dispersed in a single cell suspension. The sample can be obtained from any site which contains peripheral mononuclear cells and must contain a quantity of mononuclear cells such that after culturing there is an adequate number of cells to be analyzed. Density gradient centrifugation techniques, e.g. ficoll-hypaque separation, can be utilized to increase the percentage of mononuclear cells. This technique is especially important for samples with disproportionate numbers of granulocytes, e.g. peripheral blood from subjects having an acute bacterial infection or from subjects having a disease which suppresses the number of mononuclear cells.

The sample of isolated cells is cultured with a standard stimulus for a period of time sufficient to allow a measurable amount of activation antigen expression, as influenced by mononuclear cell subclass interaction, to develop. In this particular embodiment, the isolated cells at a concentration of 1 million cells per milliliter are cultured with PHA at a concentration of 37.5 micrograms per milliliter, serving as a standard stimulus, for 18 hours. RPMI 1640 with fetal calf serum and glutamine serve as a culture media. The culture time is determined for each particular standard stimulus using samples from normal subjects, culturing portions of each sample for different lengths of time and determining the amount of activation antigen expression for each culture time. A measurable amount of IL-2 receptor expression is observed about 18 hours after initiating the culture with PHA. The 18 hour culture period facilitates the use of this invention as a clinical assay.

After culturing, the cells are washed to remove the standard stimulus and then aliquots of cells are simultaneously incubated with two monoclonal antibodies, each directly conjugated to different fluorometrically distinguishable fluorophores. The first fluorophore-conjugated monoclonal antibody binds to a select mononuclear cell subclass antigenic determinant and the second fluorometrically distinguishable fluorophore-conjugated monoclonal antibody binds to a select cell surface activation antigen. After incubation, the cells are washed to remove excess antibody and, in this particular embodiment, fixed with 1% paraformaldehyde to halt any further cellular activity.

It should be noted that a portion of the isolated cells can be obtained prior to culturing. Aliquots of these cells can be incubated with monoclonal antibodies and prepared as described above. These aliquots of cells can then be used to measure data parameters which might be effected by culturing with a standard stimulus, e.g. the degree of cellular activation prior to culturing. Culturing with a standard stimulus can also effect changes in cell morphology and antigenic determinant modulation.

In a preferred embodiment, the first fluorophore which is conjugated to a monoclonal antibody is FITC and the second fluorometrically distinguishable fluorophore is PE. Data concerning the amount of green and red fluorescence emitted by a particular cell as it passes the light beam allows for a determination of the amount of specific subclass antigenic determinants and activation antigens expressed on the cell. When examining fluorescence data from cells with approximately the same surface area (e.g. those cells within an area of interest), the amount of antigenic determinant or activation antigen expressed can be referred to as a density.

In this particular embodiment, direct fluorophore-conjugated monoclonal antibodies are used to identify and enumerate cell surface antigens including anti-Leu-3a-FITC, anti-Leu-2a-FITC and anti-IL2R-PE (Beckton Dickinson, Mountain View, Calif.). Examples of alternative fluorophore-conjugated monoclonal antibodies include, but are not limited to: anti-Leu-4-FITC, anti-Leu-12-FITC, anti-Leu-11-FITC and anti-OKT9-PE.

In this particular embodiment, an EPICS V flow cytofluorometer (Coulter Corporation, Hialeah, Fla.) is used to collect four parameter data consisting of forward light scatter, orthogonal light scatter, green fluorescence (515–535 nm) and red fluorescence (>590 nm). An Inovax coherent argon laser emitting 400 milliwatts of power at a wave length of 488 is was used as an excitation source. A threshold trigger for forward light scatter is used to exclude red blood cells and debris. The gain for the forward light scatter detector amplifier is set at 5. A neutral density filter is placed before the forward light scatter detector.

A collection lens, set orthogonally to the intersection of the laser beam and fluid stream, passes light to a series of filters and beam splitters. The following filters and beam splitters are used: 488 dichroic (long pass) to reflect light to the orthogonal light scatter detector, a 515 interference long pass, a 560 dichroic (short pass) to reflect light to the red fluorescence detector, 590 long pass for red fluorescence and 525 band pass for green fluorescence. The PMT used to detect orthogonal light scatter is set at an applied high voltage of 330. The PMTs used to detect green and red fluorescence are both set at an applied high voltage of 650. The signals, from the orthogonal light scatter detector and from the green and red fluorescence detectors, are applied to integrators and then logarithmic amplifiers. Prior to logarithmic amplification, a compensation network to correct for overlap of the emission spectra of the fluorophores is used to subtract 30% of the green signal from the red signal and 20% of the red signal from the green signal for each cell. Subtraction values are established using aliquots of stimulated mononuclear cells incubated with single fluorescent probes, e.g. anti-Leu-3-FITC and anti-IL2R-PE. It should be noted that the filters and settings listed above are exemplary and are not intended to limit the scope of the invention. However, when comparing samples, the same particular embodiment of the method should be used for each sample.

Figure 2:
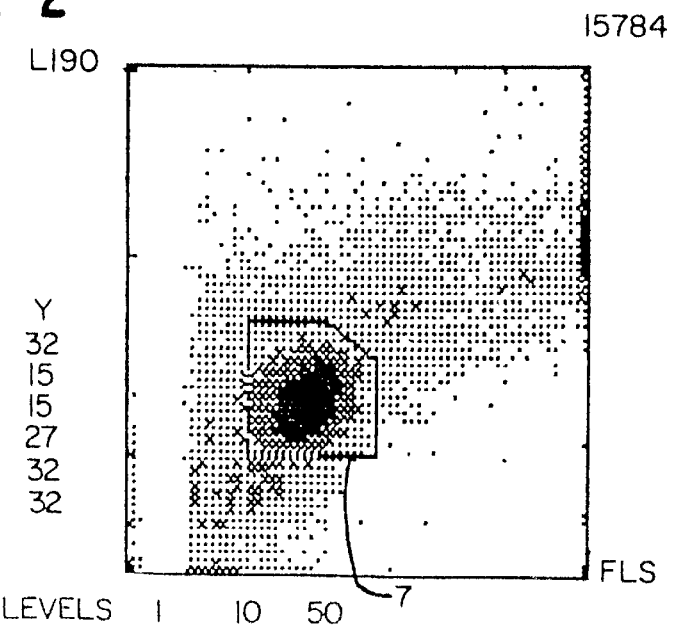
FIG. 2 shows a histogram of forward light scatter and orthogonal light scatter data as measured by a flow cytofluorometer of the same leukocytes as in FIG. 1 with one area of interest demarcated.

The FIGS. 1–11 and data presented for illustrative purposes in this detailed description constitute an example of the assessment of the immunoregulatory status of the mononuclear leukocyte immune system of an organ transplant patient. A sample was obtained as described above. FIGS. 1 and 2 are from an aliquot of cells obtained prior to culturing with a standard stimulus. FIGS. 3–11 are from aliquots processed after culturing with PHA for 18 hours. The analysis of these histograms was performed using the MDADS software package (Coulter Corporation, Hialeah, Fla.).

In FIG. 1, we can see a histogram wherein forward and orthogonal light scatter is employed to differentiate lymphocytes, monocytes and residual granulocytes in an aliquot from a sample of substantially mononuclear cells obtained by ficoll-hypaque isolation of peripheral blood from a liver transplant patient. These cells have not been cultured with a standard stimulus. Using the two light scatter parameters the major cellular components of the immune system are differentiated. Orthogonal light scatter is proportional to the intracellular structure, while forward light scatter is proportional to the size or diameter of the cell. The light scatter "areas of interest" demarcated by the solid lines forming geometric shapes are indicative of the different leukocyte classes. The granulocyte class is substantially identified by Box 2. The monocyte class is substantially identified by Box 3. The lymphocyte class is substantially identified by Box 4. An aliquot of cells obtained prior to culturing can be used to determine the quantity of cells in particular classes of leukocytes present in the sample of isolated cells by integrating for the number of cells in each area of interest.

An aliquot of cells obtained prior to culturing with a standard stimulus can be used to adjust a preset light scatter area of interest for variations in alignment of the flow cytofluorometer. The preset light scatter area of interest is demarcated using forward and orthogonal light scatter data collected from aliquots of cells from normal individuals. Due to changes in cell morphology (e.g. cell death or the development of lymphoblasts) with increasing time in culture which make the distinction between cell classes less clear on the histogram, the preset light scatter area of interest is adjusted using an aliquot of cells obtained prior to culturing. This adjusted area of interest is then used to analyze all aliquots of the sample, including those obtained after culturing. In cases where the entire sample must be put into culture due to low cell number, the preset light scatter areas of interst is used to analyze the aliquots of cells.

FIG. 2 shows the same histogram as in FIG. 1 except that only the area of interest indicative of lymphocytes is identified, i.e. Box 7 (the same as Box 4 in FIG. 1). The x and y coordinates of the points used to generate the geometric shape are listed to the left of the histogram. These are the coordinates of the preset light scatter area of interest substantially identifying lymphocytes used in this particular embodiment. There was no adjustment of the preset light scatter area of interest for this sample. Of the 15,784 total cells represented on the histogram, 10,132 cells or 64.19 percent are within the area of interest which substantially identifies lymphocytes.

By measuring the two light scatter and two fluorescent parameters, the flow cytofluorometer generates four parameter data on individual cells which can be analyzed to determine activation antigen expression on cells of a select mononuclear cell subclass. When this four parameter data for individual cells is grouped for all of the cells of the aliquot for which data was generated, it is termed cumulative four parameter data. Analysis of the cumulative four parameter data for an aliquot of mononuclear cells identifies cells of a select mononuclear cell class(es) using light scatter area(s) of interest, e.g. lymphocytes and/or lymphoblasts. Cells of the particular class(es) are then analyzed to determine the minimal density of antigenic determinant expression on a cell necessary to qualify the cell as a member of a select mononuclear cell subclass, the quantity of cells having greater than the minimal density of antigenic determinant, and the quantity of activated cells in said select mononuclear cell subclass having greater than a preset minimal density of activation antigen expression necessary to qualify the cell as being activated.

In a similar manner, analysis of cummulative four parameter data can be performed for aliquots of cells obtained prior to culturing with a standard simulus. It is usually assumed that there is little significant activation antigen expression prior to culturing with a standard stimulus, however in patients with certain diseases or receiving immunopotentiating medication, there could be an appreciable amount of activation antigen expression. In these cases, analysis of the degree of cellular-activation in particular subclasses should be performed prior to and after culturing with a standard stimulus such that the amount of change in cellular activation can be determined. Also, an analysis to determine the quantity of cells in particular mononuclear cell subclasses can be performed prior to culturing with a standard stimulus which can modulate the particular antigenic determinants.

Figure 3:
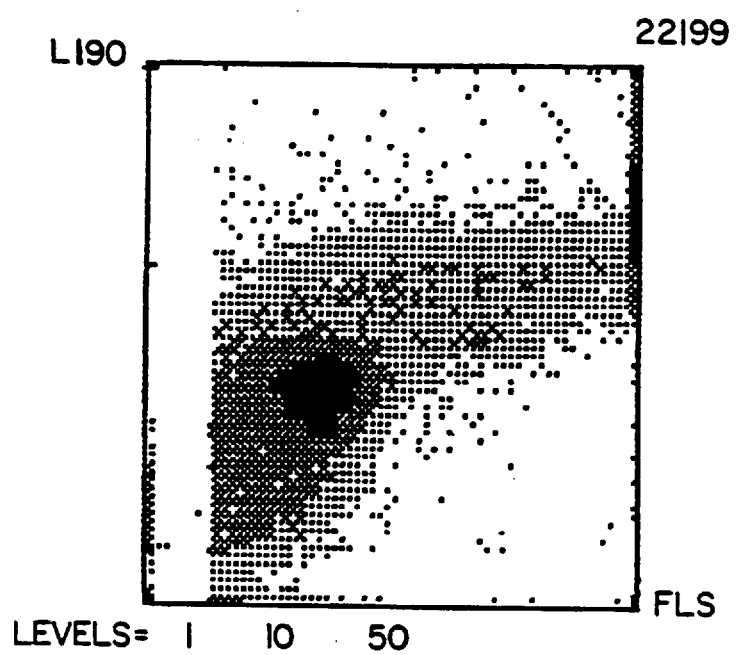
FIG. 3 shows unanalyzed two parameter light scatter data as measured by a flow cytofluorometer of leukocytes isolated from a peripheral blood sample by density gradient centrifugation after culturing with PHA for 18 hours.

FIGS. 3–9 illustrate an analysis of cumulative four parameter data for cells from an aliquot of cells cultured with PHA for 18 hours and then incubated with anti-Leu-3a-FITC and anti-IL2R-PE. In a preferred embodiment, green and red fluorescence data is analyzed for approximately 10,000 cells whose light scatter data placed them in the "lymphocyte" area of interest. This increases the statistical significance of the analysis of this data. FIG. 3 shows a two parameter histogram of unanalyzed forward and orthogonal light scatter parameters for the 22,199 cells on which data was collected.

Figure 4:
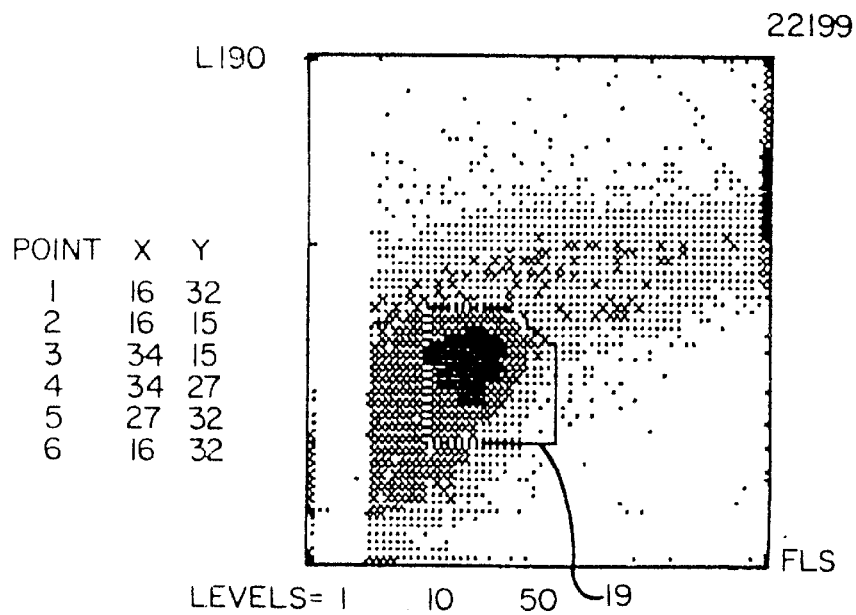
FIG. 4 shows the same data for the same leukocytes as in FIG. 3 with an area of interest indicative of lymphocytes demarcated.

FIG. 4 shows the same histogram as in FIG. 3 with the area of interest which substantially identifies lymphocytes demarcated, i.e. Box 19. The x and y coordinates of the points used to generate the geometric shape are listed to the left of the histogram. These coordinates are the same as those used to generate the shape on a similar histogram of cells prior to culturing (see FIG. 2). For every aliquot of cells from a particular sample, both before and after stimulation, the coordinates used to generate an area of interest on the forward and orthogonal light scatter histogram are the same such that the area of interest demarcates cells of similar morphology for each aliquot.

By defining a minimal (and maximal) density of specific antigenic determinant for inclusion in a certain subclass, cells can be assigned to the subclass by measuring the amount of fluorescence associated with the fluorophore-conjugated monoclonal antibody which identifies the antigenic determinant on the cell's surface. The assigned cells are referred to as being antigenic determinant positive. Also, a minimal density can be defined for activation antigen expression to determine the presence of such antigens. Certain ranges of density above this minimal are measured for certain activation antigens, e.g. IL2R, and can serve as an indirect determination of specific lympho-monokine production, e.g. IL-2.

The density of a certain specific antigenic determinant can vary somewhat between individuals or with antigen modulation, e.g. during activation. To determine the minimal density of a specific antigenic determinant for a particular aliquot of cells which have been incubated with first and second fluorophore-conjugated monoclonal antibodies, a plot of cell number versus amount of first fluorophore fluorescence is made. In this particular embodiment, the first fluorophore is FITC and it is conjugated to monoclonal antibodies identifying antigenic determinants. The second fluorophore is PE and is conjugated to monoclonal antibodies identifying activation antigens. Using only cells which have less than a certain minimal amount of red fluorescence will exclude many of the nonspecific binding cells as they will have bound both the green and red fluorescent antibodies. From the plot of cell number versus the amount of green fluorescence, an estimate of the tangent to the positive slope of the curve can be made. The curve represents an approximate gaussian distribution due to the lognormal distribution of antigenic determinants. The x-intercept generated by such a tangent will define a minimal fluorescence intensity which correlates with a minimal specific antigenic determinant density. (A similar procedure can be used to determine the maximal antigenic determinant density from the negative slope.) In this particular embodiment, the maximal density is set as the highest density which can be measured. Using these density boundaries, the two parameter histogram of green and red fluorescence can be integrated between these boundaries to enumerate the number of cells which are positive for the antigenic determinant and can be assigned to a particular subclass. It should be noted that alternative methods can be used to determine these minimal and maximal densities such that a similar number of cells will be assigned to the subclass.

A minimal density is defined to determine the presence of activation antigens. This minimal density will vary with different gain and high voltage settings for certain components of the flow cytofluorometer and the particular light source, alignment, filters and fluorescent detection electronics. Thus, it can be seen that this minimal density of activation antigen expression must be defined after determining standard settings and will be indicative of a minimal density measurable by a particular flow cytofluorometer using these settings.

An iterative analysis of samples from normal individuals, both prior to and after culturing with a standard stimulus for a certain length of time, must be performed to determine the minimal density of activation antigen measurable. This analysis uses the two parameter fluorescence data from aliquots of cells incubated with fluorometrically distinguishable fluorophore-conjugated monoclonal antibodies either to both the antigenic determinant and the activation antigen, to both the antigenic determinant and a control (e.g. non-human) antigen, or to only the antigenic determinant. From two parameter histograms a minimal fluorescent intensity indicative of activation antigen expression can be determined above which there is more specific (versus nonspecific) binding and the overlap from the emission spectra the fluorophore indicative of the antigenic determinant of is not significant (e.g. less than about 2 percent).

Thus, each aliquot is first analyzed to determine the minimal (and maximal) density of a specific antigenic determinant for inclusion in the subclass being examined and the subclass is enumerated from the two parameter fluorescence data. Then by further analyzing the two parameter fluorescence data using these densities and the preset minimal activation antigen density, an enumeration of the number of cells which belong to the subclass and have expressed activation antigen is made. In a similar way, an enumeration is made of the number of cells which belong to the subclass and have expressed activation antigens within certain preset specified density ranges. Cummulative four parameter data from an aliquot incubated with both first fluorophore- and second fluorophore-conjugated control monoclonal antibodies is analyzed using these same densities to determine the approximate number of false positives due to nonspecific binding. If the amount of nonspecific binding is significant, the results obtained from aliquots incubated with the monoclonal antibodies to antigenic determinants and activation antigens can be corrected.

It should be noted that cells with two specific antigenic determinants of known densities can be identified with two different monoclonal antibodies conjugated to the same first fluorophore such that the cumulative fluorescence emitted is equivalent to the sum of their respective densities. This technique allows further distinction of subclasses, e.g. cells having both Leu-3a and Leu-8 antigenic determinants. As above, the second fluorophore-conjugated monoclonal antibody identifies a certain activation antigen which might be expressed over a range of densities. Alternatively, three fluorometrically distinguishable fluorophore-conjugated monoclonal antibodies can be used to identify two specific antigenic determinants and an activation antigen.

Figure 5:
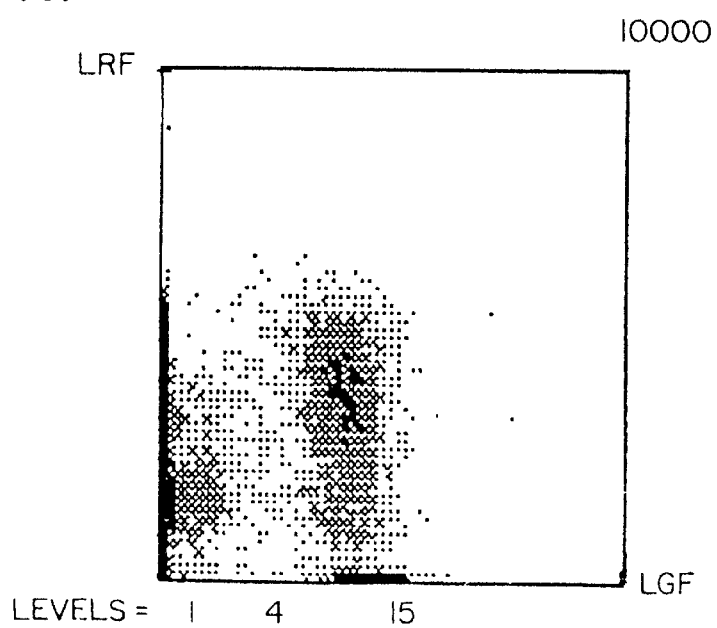
FIG. 5 shows unanalyzed two parameter fluorescence data of stimulated mononuclear cells incubated with both anti-IL2R-PE and anti-Leu-3a-FITC and determined to be lymphocytes as in FIG. 4.

In this particular embodiment, green and red fluorescence data is analyzed only for cells meeting the forward and orthogonal light scatter criteria as defined by the area of interest substantially identifying the lymphocytes. FIG. 5 shows a two parameter histogram of unanalyzed green and red fluorescence data parameters of the leukocytes identified to be lymphocytes in FIG. 4. The green and red fluorescence intensities relate to the number of excited fluorophores bound to the cell by the monoclonal antibodies anti-Leu-3a-FITC and anti-IL2R-PE, respectively.

Figure 6:
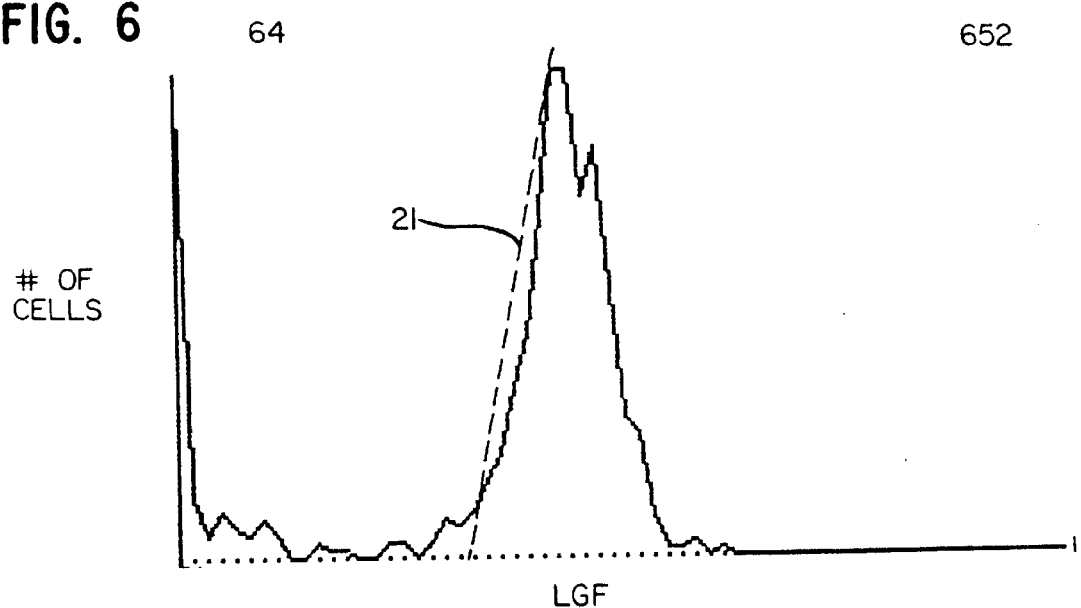
FIG. 6 shows a histogram of green fluorescence data constructed using only those cells in the zero and one red fluorescent channels from FIG. 5.

In this particular embodiment, a plot of cell number versus the amount of green fluorescence is constructed using only those cells in the zero and one red fluorescence channels. An estimate of the tangent to the positive slope of the curve is made. The x-intercept generated by this tangent defines the minimal specific antigenic determinant density. FIG. 6 shows a one parameter histogram of the green fluorescence data parameter of the lymphocytes for which the amount of red fluorescence measured placed them in the 0 or 1 channel on the LRF axis. An approximate bell-shaped curve is generated. An approximation of the tangent to the positive slope of the curve is used to generate a line, 21. It should be noted that the curve can be processed using computerized smoothing techniques to facilitate this approximation. The approximate x-intercept of the line, channel 20, is used as the channel number at which to draw a cursor line on the two parameter histogram in FIG. 7. This is considered the minimal density of antigenic determinant expression which a cell must have to qualify as a member of the select mononuclear subclass, which the antigenic determinant defines.

Figure 7:
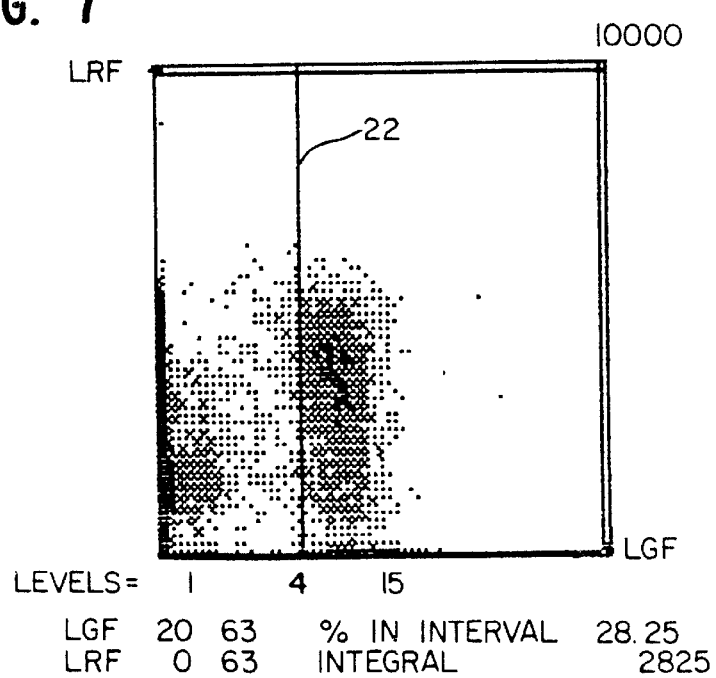
FIG. 7 shows the same data for the same leukocytes as in FIG. 5 with a cursor line set at the approximate x-intercept as determined in FIG. 6.

A cursor is set on the green and red fluorescence data histogram using the x-intercept. FIG. 7 shows the same two parameter histogram as in FIG. 5 with a cursor line 22, set at LGF channel 20 as determined in FIG. 6. As shown in FIG. 7, the area of interest used to determine the percentage of lymphocytes which can be assigned to the subclass identified by antigenic determinant Leu-3a, i.e. Leu-3a positive cells (hereinafter Leu-3a+), is between LGF channels 20 and 63. The percentage of lymphocytes as identified in FIG. 7 which are Leu-3a+ is 21.81.

Figure 8:
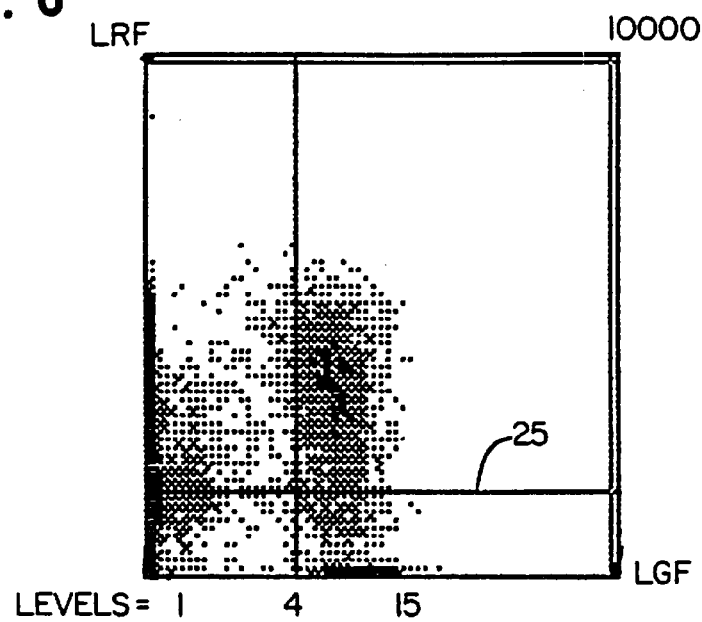
FIG. 8 shows the same data for the same leukocytes as in FIG. 7 with a second cursor set at the red fluorescence channel 10.

In this particular embodiment, a red fluorescence cursor is set at channel 10 on the green and red fluorescence data histogram and the number of total cells, i.e. lymphocytes, which are activated and are assigned to the subclass identified by the antigenic determinant is determined. A LRF channel at 10 was chosen to represent the minimal amount of IL-2 receptor which a cell must express to be considered activated, after an iterative analysis as detailed above. FIG. 8 shows the same two parameter histogram as in FIG. 7 with a second cursor line, 25, set at LRF channel 10. As shown in FIG. 8, the area of interest used to determine the percentage of lymphocytes which are Leu-3a+ and express greater than the minimal amount of IL-2 receptor (hereinafter IL2R+) is between LGF channels 20 and 63, and LRF channels 10 and 63. The percentage of lymphocytes which are Leu-3a+ and IL2R+ (or Leu-3a+IL2R+) is 20.67.

Figure 9:
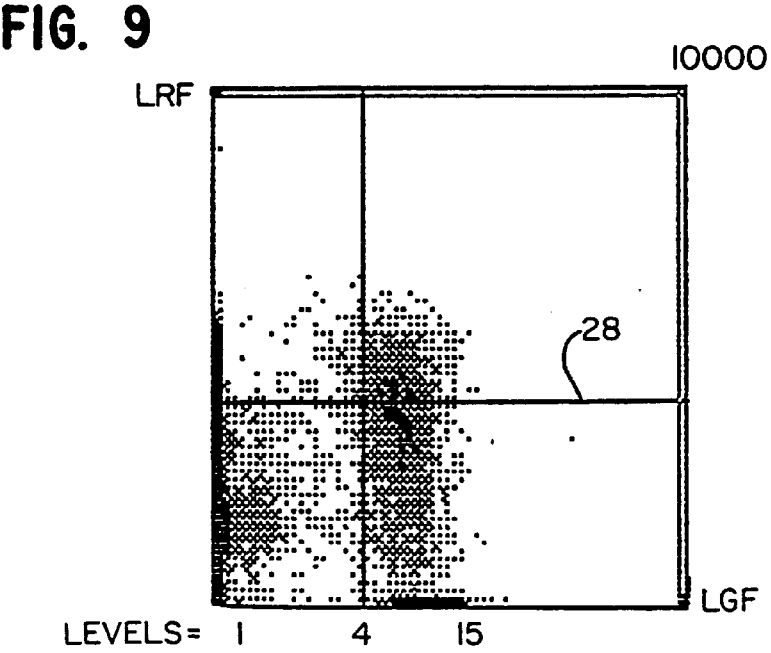
FIG. 9 shows the same data for the same leukocytes as in FIG. 7 with a third cursor set at the red fluorescence channel 25.

In this particular embodiment, a red fluorescence cursor is set at channel 25 on the green and red fluorescence data histogram to distinguish different density ranges of IL-2 receptor expression on cells which are members of a select subclass. The quantity of lymphocytes which are members of a select subclass and have a high density of IL-2 receptor expression is determined. The channel number 25 was determined using an iterative analysis of samples from normal individuals cultured for 48 hours to examine for the average density range present on such cells. A LRF channel of 25 was chosen to represent the lowest density of IL-2 receptors which a cell must express to be considered to have a high density of IL2R on its cell surface. FIG. 9 shows the same two parameter histogram as in FIG. 7 with a third cursor line, 28, set at LRF channel 25. As shown in FIG. 9, the area of interest used to determine the percentage of lymphocytes which are Leu-3a+ and express a high density of IL-2 receptor is between LGF channels 20 and 63 and LRF channels 25 and 63. The percentage of lymphocytes which are Leu-3a+ and express a high density of IL-2 receptor is 8.16.

A similar analysis of cumulative four parameter data as that shown in FIGS. 3–9 can be performed for each aliquot from the sample of peripheral mononuclear cells.

Figure 10:
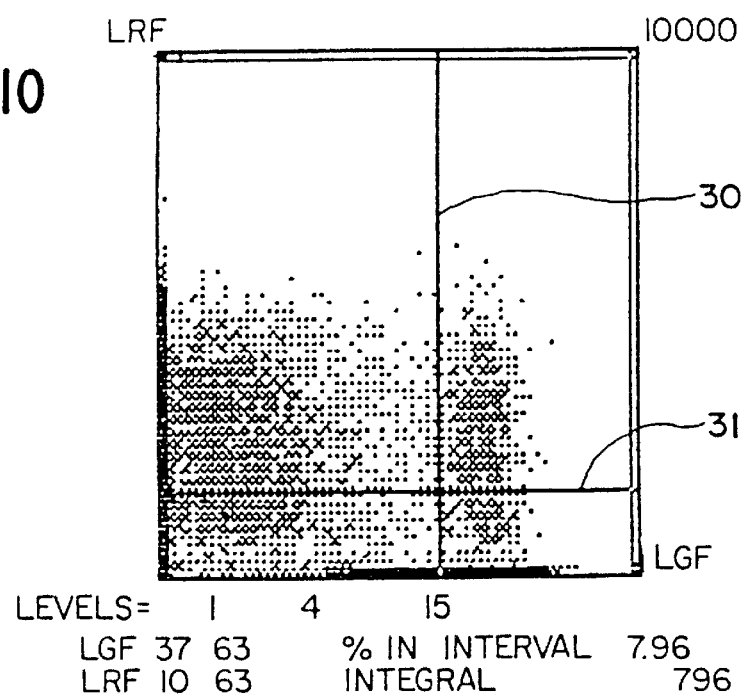
FIG. 10 shows two parameter fluorescence data of stimulated mononuclear cells incubated with both anti-IL2R-PE and anti-Leu-2a-FITC and determined to lymphocytes similarly to FIG. 4. With cursors set in a similar manner as in FIG. 8.

In this particular embodiment, cells with a high density of Leu-2a antigenic determinants are considered to be of the suppressor cytotoxic T-cell subclass. FIG. 10 shows a two parameter fluorescence data histogram similar to that in FIG. 8 for an aliquot of cells from the same sample and which was incubated with anti-Leu2a-FITC and anti-IL2R-PE. The green fluorescence cursor 30 is set at channel 37 and the red fluorescence cursor 31 is set at channel 10 on the green and red fluorescence data histogram. The area of interest used to determine the percentage of lymphocytes which are Leu-2a+ and IL2R+ is between LGF channels 37 and 63 and LRF channels 10 and 63. The percentage of lymphocytes which are Leu-2a+ and IL2R+ is 7.96.

The occurrence of nonspecific binding of the monoclonal antibodies, which often increases with the time spent in culture, varies for the different leukocyte classes. Granulocytes and monocytes have relatively higher densities of nonspecific binding sites on their cell surfaces than do lymphocytes. This nonspecific binding makes accurate cytofluorometric measurement of activated cells more difficult as the average density of nonspecific binding sites nears that of the antigenic determinants and activation antigens. An accurate determination, however, can be made using forward and orthogonal light scatter parameters to delineate the leukocyte classes and excluding the classes with high densities of nonspecific binding sites when analyzing fluorescence data for lymphocytes which have low densities of such sites. It should be noted that an unconjugated monoclonal antibody with high affinity for a nonspecific binding site, e.g. anti-Leu-11 for the granulocyte and natural killer cell Fc receptor or a monoclonal antibody to the monocyte Fc receptor, can be used to block the site's low affinity non-specific binding with other monoclonal antibodies.

Figure 11:
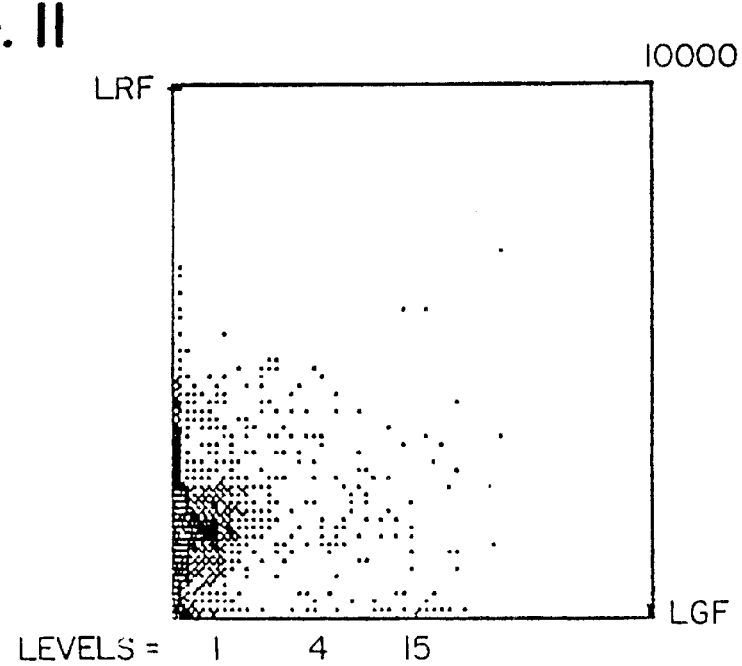
FIG. 11 shows unanalyzed two parameter fluorescence data of stimulated mononuclear cells incubated with both mouse-IgG$_1$-PE and mouse-IgG$_1$-FITC and determined to be lymphocytes similarly to FIG. 4.

In a similar manner to the analyses described above, fluorophore-conjugated control monoclonal antibodies directed against antigens not found in the human immune system can be used to determine the number of cells with a significantly high quantity nonspecific binding site densities such that these cells are in the areas of interest. FIG. 11 shows a two parameter histogram of unanalyzed green and red fluorescence data parameter data of the leukocytes identified to be lymphocytes similar to FIG. 4. The green and red fluorescence intensities relate to the number of excited fluorophores bound to the cell by the control monoclonal antibodies, mouse-IgG$_1$-FITC and mouse-IgG$_1$-PE, respectively (Becton Dickinson, Mountain View, Calif.). The same areas of interest as used in FIGS. 7–10 were applied to this histogram thereby determining an approximate number of false positives in each area of interest which is due to nonspecific binding. This allows for correction of the percentages determined for each area of interest in FIG. 7–10.

From the analysis of cumulative four parameter data for each aliquot, the degree of cellular activation of each mononuclear cell subclass can be determined. This can be used to assess the immunoregulatory status of the mononuclear leukocyte immune system of the sample of peripheral mononuclear cells and can be correlated with the in vivo immunoregulatory status of the patient as determined clinically. In this illustration of a preferred embodiment, the degree of cellular activation for each subclass is determined using the percentage of a select subclass which are activated and ratios of the percentage of activation for the different subclasses. This is utilized to clinically assess the immunoregulatory status of the mononuclear leukocyte immune system of liver transplant patients. In this example, the percentage of cells of a select mononuclear cell subclass which are activated, i.e. express greater than the preset minimal IL-2 receptor density, are termed "Activated Leu-3a+", etc.

Peripheral blood samples were obtained from liver transplant recipients sequentially over a period of four months after receiving the transplant. Ten normal individuals served as controls. Mononuclear leukocytes from each sample were isolated, cultured, incubated with monoclonal antibodies and four parameter data collected and analyzed as described above. Certain results for the patient sample illustrated in FIGS. 1–11 are found in Table I.

TABLE I

|  | Activated Leu-3a+ | Activated Leu-2a+ | Ratio Activated Leu-3a+: Activated Leu-2a+ |
| --- | --- | --- | --- |
| Liver Transplant Recipient A | 73 | 26 | 2.8 |

From Table I it is seen that 73 percent of the patient's helper/inducer lymphocytes became activated as measured by IL-2 receptor expression after culturing with PHA for 18 hours. Similarly, 26 percent of the patient's cytotoxic/suppressor T lymphocytes became activated. The ratio of the percent activation of the two subsets was 2.8.

The results of the present assay were correlated with liver biopsy pathologic determinations of rejection obtained on the same day as the samples. The morphologic criteria for a diagnosis of "no rejection" included normal or mild nonspecific portal inflammation consisting mainly of lymphocytes. The morphologic criteria for a diagnosis of "rejection" included inflammatory infiltrate of triads with lymphocytes and plasma cells resulting in piecemeal necrosis, disorganization and degenerative changes of bile duct epithelium, and phlebitis of central veins. A diagnosis of "suspicious" was given to those samples with partial criteria for a diagnosis of rejection.

The results of the generated and analyzed four parameter data from aliqouts of samples from liver transplant recipients are summarized in Table II. Samples were included in the "No Rejection" category on the table if the corresponding biopsy had a diagnosis of "no rejection" and the sample was not obtained within 7 days of transplant surgery or within 10 days of a "suspicious" or "rejection" biopsy diagnosis. The samples in the "Rejection" category were obtained from patients who were on stable doses of immunosuppressive medications (glucocorticoids and cyclosporin) and had a corresponding biopsy diagnosis of "rejection".

TABLE II

|  | Activated Leu-3a+ | Activated Leu-2a+ | Ratio Activated Leu-3a+: Activated Leu-2a+ |
|---|---|---|---|
| Normals (n = 10) | 75 ± 6* | 11 ± 4 | 4 to 14 |
| Liver Transplant Recipients No Rejection (n = 13) | 61 ± 18 | 9 ± 8 | 2.8 to 15 |
| Rejection (n = 6) | 80 ± 9 | 37 ± 13 | 1.5 to 3.0 |

*mean ± 0 standard deviation.

It can be seen from the summarized results in Table II that liver rejection correlates with a higher percent of activated Leu-2a+ lymphocytes, i.e. the altered immunoregulatory status can be assessed from the degree of Leu-2a+ cellular activation. Therefore, using the methods described herein the clinician can assess the immunoregulatory status of the mononuclear leukocyte immune system to facilitate the diagnosis of transplanted organ rejection.

Example 2

This example shows an analysis of the immunoregulatory status of the mononuclear leukocyte immune system of patients receiving immunosuppression therapy. Peripheral blood samples were obtained from ten normal individuals and six liver transplant recipients. The transplant recipients are divided into 2 groups. The first group consists of 4 patients who did not have a rejection episode in their four to eight week post-transplant hospital course. The second group consists of two patients with two sequential samples both with corresponding biopsy dianosis of "rejection".

Peripheral blood mononuclear leukocytes from each sample were isolated by density gradient centrifugation, cultured with PHA for 18 hours, incubated with monoclonal antibodies and four parameter data collected and analyzed as described in "Detailed Description". Unless otherwise noted, all samples were obtained from the patients about one hour prior to receiving their immunosuppressive medication. Biopses were obtained and pathologic determinations done as described above.

Each normal had one sample drawn while each of the first group of transplant recipients had four to eight samples drawn on different dates during their four to eight week post-transplant hospital course. During their hospital course, the patients were treated with cyclosporin and corticosteroids for immunosuppressive therapy. Cyclosporin blood levels were monitored using the HPLC method. G. L. Lensmeyer and B. L. Fields, "Improved Liquid-Chromatographic Determination of Cyclosporin, with Concomitant Detection of a Cell-Bound Metabolite," *Clinical Chemistry*, (31) 196–201 (1985). During their hospital course there were certain changes in the cyclosporin dose, cyclosporin level and/or corticosteroid dose.

The pertinent clinical data and results are summarized in Table III. The following should be noted: all cyclosporin doses were converted to the equivalent intravenous dose using a conversion factor of ⅓ for oral doses (Physician's Desk Reference, 1986) and all glucocorticoid doses were converted to the predisone equivalent (p. 365, *Manual of Medical Therapeutics,* 1983). All samples are grouped by patient to facilitate analysis of changes in immunosuppressive therapy. Also, all samples are listed sequentially starting approximately one week after receiving the liver transplant. Samples were obtained every three to seven days. For those patients tested, the values for the analysis of samples obtained prior to transplant approximated the normal values.

TABLE III

| Patient | Cyclosporin Dose | Cyclosporin Blood Level | Prednisone Dose | Activated* Leu-3a+ | % of Activated Leu-3a+ expressing a high density of IL2R |
|---|---|---|---|---|---|
| Normal (n = 10) | 0 | 0 | 0 | 75 ± 6** | 40 ± 9 |
| G(n = 4) | 120 | 228 ± 42 | 25 | 7 | 14 |
|  |  |  | 20(n = 3) | 28 ± 4 | 17 ± 1 |
| H(n = 8) | 80 | 122 ± 31 | 38 | 15 | 13 |
|  |  |  | 25(n = 5) | 35 ± 8 | 31 ± 6 |
|  |  |  | 20(n = 2) | 74 ± 5 | 31 ± 6 |
| I(n = 4) | 180(n = 2) | 176 ± 40 | 20 | 62 ± 4 | 16 ± 11 |
|  | 170(n = 2)*** | 408 ± 106 |  | 13 ± 4 | 14 ± 7 |
| J(n = 8) | 200 | 254 | 50 | 45 | 31 |
|  | 200 | 126 | 38 | 59 | 32 |
|  | 200 | 101 | 25 | 73 | 38 |
|  | 125 | 100 | 19 | 81 | 36 |
|  | 125 | 90 | 19 | 73 | 38 |
|  | 75 | 43 | 13 | 73 | 66 |
|  | 75 | 51 | 0 | 77 | 65 |
|  | 75 | 0 | 0 | 88 | 63 |

*Activated Leu-3a+ = the percentage of Leu-3a+ which express greater than the minimal IL-2 receptor density.
**Mean ± standard deviation
***This patient had unexpectedly high oral absorption increasing his blood level.
Cyclosporin dose = mg every 12 hours, level is ng/ml
Prednisone dose = mg every 24 hours.

From this study it can be seen that the method described herein detects changes in the immunoregulatory status due to immunosuppressive therapy. From the summarized results in Table III, it can be seen that changes in immunosuppressive therapy have a negative correlation with changes in the percent of activated Leu-3a+ lymphocytes and of activated Leu-3a+ expressing a high density of IL-2 receptor, e.g. increases in immunosuppressive therapy yields a decrease in activated Leu-3a+. In patients G and H, the cyclosporin dose and levels were approximately constant while the glucocorticoid (predisone) dose was decreased. It is seen that the percent of activated Leu-3a+ lymphocytes increases with decreasing doses of glucocorticoids in these patients. In patient I there was unexpectedly high oral absorption of cyclosporin when the patient was converted from intravenous to oral doses. The patient's cyclosporin level increased while the glucocorticoid dose remained constant. It is seen that the percent of activated Leu-3a+ lymphocytes decreased with increased blood levels of cyclosporin in this patient. In patient J, eight samples are listed sequentially showing decreasing cyclosporin dose, cyclosporin level and glucocorticoid dose. It can be seen that the percent of activated Leu-3a+ lymphocytes increases with the decreasing level of immunosuppressive therapy in this patient. It can also be seen that as the cyclosporin level and glucocorticoid dose near zero that the percent of activated Leu-3a+ lymphocytes expressing a high density of IL-2 receptors increases, possibly related to the release of the suppression of IL-2 production by the immunosuppressive medications. The increased level of IL-2 production would thereby unregulate the IL-2 receptor.

The results from the samples drawn from the second group of transplant recipients show the acute effects of immunosuppressive therapy even during rejection episodes. The pertinent clinical data and results are summarized in Table IV.

of immunosuppressive therapy on the immunoregulatory status of the mononuclear leukocyte immune system of patients. By delineating a select mononuclear cell subclass, this assay can facilitate the targeting of immunosuppresive or immunopotentiating therapy for a particular subclass. Also, alterations of the methods described herein, e.g. using serum from a patient on immunosuppressive or immunopotentiating therapy in the culture, can facilitate a refinement of the assessment of the effects of a patient's medication on the immunoregulatory status and are within the scope of this invention.

Example 3

This example shows an analysis of T lymphocyte antigenic determinant expression, IL-2 receptor expression and IL-2 receptor expression on T lymphocyte antigenic determinant positive mononuclear cells. This analysis is correlated with the stimulation index as measured by a 72 hour PHA culture with tritiated thymidine uptake. Peripheral blood mononuclear cells from normal donors were isolated by density gradient centrifugation, cultured with PHA, incubated with monoclonal antibodies to select mononuclear cell subclass antigenic determinants and to IL-2 receptors and four parameter data generated and analyzed similar as described in "Detailed Description". Monoclonal antibodies used included FITC-conjugated antibody for the antigenic determinants Leu-4, Leu-3a or Leu-2a, and PE-conjugated monoclonal antibody for IL-2 receptor. Four parameter data was collected on cells using an EPICS-V flow cytofluorom-

TABLE IV

| Patient | Cyclosporin Dose | Cyclosporin Blood Level | Prednisone Dose | Activated* Leu-3a+ | % of Activated Leu-3a+ expressing a high density of IL2R |
|---|---|---|---|---|---|
| A | 68 | 200 | 15 | 73 | 39 |
| A** | 68 | N.D. | 15 | 66 | 10 |
| B | 150 | 217 | 25 | 91 | 69 |
| B*** | 150 | 325 | 1,250 | 82 | 38 |

*See Table III for description.
**This sample was drawn about 2 hours after the patient had received his immunosuppressive medication.
***This sample was drawn about 18 hours after the patient had received a very large dose of corticosteroids.
N.D. = not done
Cyclosporin dose = mg every 12 hours, level is ng/ml.
Prednisone dose = mg every 24 hours.

The methods described herein detect changes in the immunoregulatory status due to the acute effects of immunosuppressive therapy even during rejection episodes. The acute effects of immunosuppressive therapy correlate with a decrease in the percent of activated Leu-3a+ lymphocytes expressing a high density of IL-2 receptor.

Figure 12:
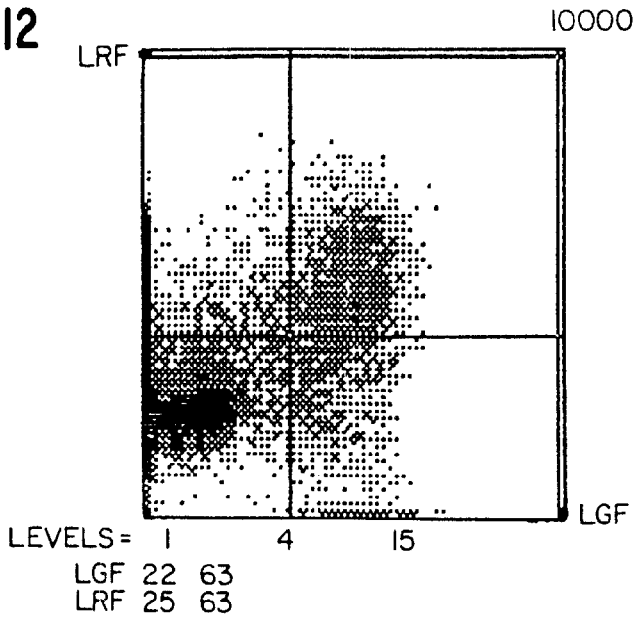
FIG. 12 shows a histogram similar to FIG. 9.
Figure 12A:
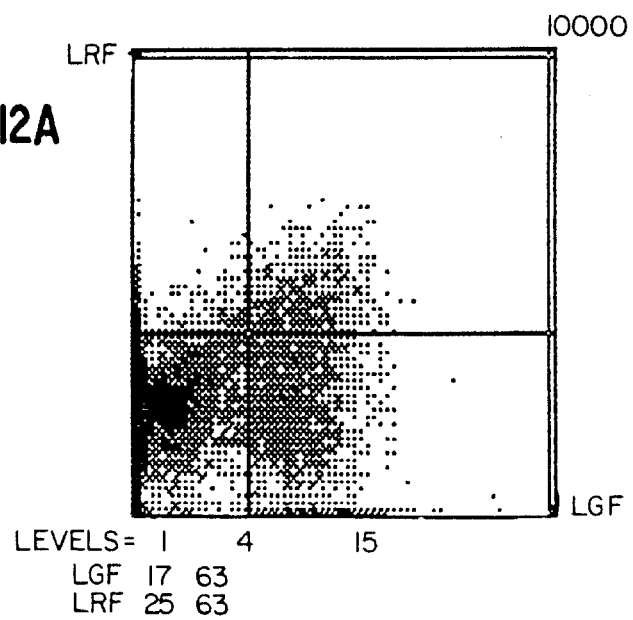
FIG. 12A shows a histogram similar to FIG. 9.

FIGS. 12 and 12A show histograms similar to FIG. 9, generated from the samples from patient B listed in Table IV. By comparison, it is seen that the density distribution of IL-2 receptor on the Leu-3a+ subclass is different for these two samples from the same subject on different dates. FIG. 12A was generated from the sample drawn 18 hours after the large does of glucocorticoids. Analysis of the four parameter data used to generate FIG. 12 revealed that 29.55 percent of the cells were Leu-3a+, 26.87 percent of the cells were Leu-3a+ and IL2R+, and 18.49 percent of the cells were Leu-3a+ and expressed a high density of IL2R. A similar analysis of the four parameter data used to generate FIG. 12A yielded 29.59, 22.93 and 7.80 percent, respectively.

The results shown in this example illustrate that the methods described herein can be used to monitor the effects eter (Coulter Corporation, Hialeah, Fla.) configured as described in "Detailed Description" with the following modification: the argon laser was used at 500 milliwatts. Forward and orthogonal light scatter parameters were analyzed to determine if the cell was within an area of interest which substantially included lymphocytes, lymphoblasts and monocytes. Green and red fluorescence data analysis was performed for such cells. The percentage of antigenic determinant and/or IL-2 receptor positive mononuclear cells, i.e., Leu-4+, Leu-3a+, Leu-2a+, IL2R+, leu-4+IL2R+, Leu-3a+IL2R+and Leu-2a+IL2R+, was determined as per the methods described herein. The results were not corrected for non-specific binding.

First, mononuclear cell subclass antigenic determinant and activation antigen analysis of PHA stimulated mononuclear cells was conducted using aliquots incubated with only one monoclonal antibody. The results are summarized in Table V.

TABLE V

| | Time in Culture with PHA (in hours) | | | |
|---|---|---|---|---|
| | 0 | 18 | 24 | 48 |
| Leu 4+ | 68 ± 2.7* | 79 ± 2.4 | 77 ± 1.9 | 81 ± 2.2 |
| Leu 3a+ | 47 ± 2.9 | 54 ± 1.7 | 54 ± 1.3 | 53 ± 2.8 |
| Leu 2a+ | 13 ± 0.7 | 18 ± 1.0 | 18 ± 0.7 | 19 ± 2.0 |
| IL2R+ | 6 ± 1.2 | 61 ± 1.9 | 71 ± 1.9 | 80 ± 1.5 |

*Expressed as percentage positive ± standard error. N = 9.

From the above study of cells stimulated for various times, as long as 48 hours, it was found that there was significant interleukin-2 receptor expression as early as 18 hours after initiating activation. At about 18 hours it was observed that nearly 60% of the mononuclear cells in the area of interest expressed IL-2 receptors.

Analysis of the PHA stimulated mononuclear cells was conducted using aliquots incubated with a FITC-conjugated monoclonal antibody to detect antigenic determinants and anti-IL2R-PE. The results are summarized in Table VI.

TABLE VI

| | Time in Culture with PHA (in hours)* | | | |
|---|---|---|---|---|
| | 0 | 18 | 24 | 48 |
| Activated Leu-4+** | 1 ± 0.3 | 49 ± 6.1 | 62 ± 3.7 | 72 ± 5.5 |
| Activated Leu-3a+ | 3 ± 1.7 | 49 ± 8.9 | 62 ± 8.5 | 70 ± 9.5 |
| Activated Leu-2a+ | 2 ± 0.8 | 25 ± 6.4 | 32 ± 4.5 | 55 ± 8.0 |

*At 72 hours post stimulation the stimulation index was determined using tritiated thymidine uptake (cpm stimulated/cpm unstimulated cells). The result was: 367 ± 88. (For comparison, the result at 18 hours was 2.75 ± 0.25).
**Percentage of antigenic determinant positive cells which express greater than the preset minimal IL-2 receptor density.

These data support previous studies that PHA preferentially activates helper/inducer T-cells as shown in this example by mononuclear cells which are Leu-3a+. It should be noted that the four parameter data used in this example was analyzed using a light scatter area of interest which susbstantially identified all mononuclear cells, therefore the results for activated Leu-3a+ and activated Leu-2a+ (Tables VI, VII) are not identical to results determined using a light scatter area of interest identifying lymphocytes. Analysis of IL-2 receptor expression on antigenic determinant positive mononuclear cell gives more information concerning the kinetics of the mononuclear cell response to mitogens than does conventional tritiated thymidine uptake.

An Activated Leu-3a+:Activated Leu-2a+ ratio greater than 1.4 correlated with a high stimulation index (hereinafter SI) to PHA (>400). Cells from one subject had a SI of 8 and a ratio of approximately 1.0 suggesting that one could predict mononuclear cell proliferating ability as measured using the SI determined at 72 hours by measuring IL-2 receptor expression on antigenic determinant positive mononuclear cells at 18 hours to compute a ratio. This relationship is summarized in Table VII.

TABLE VII

| | | 0+ | 18 | 24 | 48 | SI at 72 |
|---|---|---|---|---|---|---|
| Subject D: | Activated Leu-4+* | 1 | 68 | 75 | 84 | 535 |
| | Activated Leu-3a+ | 7 | 74 | 79 | 92 | |
| | Activated Leu-2a+ | 1 | 32 | 32 | 76 | |
| | ratio** | 2.31 | | | | |
| Subject N: | Activated Leu-4+ | 1 | 32 | 59 | ND | 8 |
| | Activated Leu-3a+ | 1 | 31 | ND | 44 | |
| | Activated Leu-2a+ | 2 | 30 | ND | 71 | |
| | ratio | 1.03 | | | | |

+Hours in culture with PHA.
*Percentage of antigenic determinant positive cells which express greater than the preset minimal IL-2 receptor density.
**At 18 hours the ratio of Activated Leu-3a+: Activated Leu-2a+ cells was determined for each sample.

From the above, it is seen that there is a differential activation of antigenic determinant positive mononuclear cells stimulated with PHA which can be measured by examining IL-2 receptor expression on such cells. Analysis of IL-2 receptor expression on these mononuclear cells after PHA stimulation gives a better understanding of the kinetics of the cellular activation in the mononuclear leukocyte immune system.

Example 4

This example shows analysis of IL-2 receptor expression on the lymphocyte class compared to IL-2 receptor expression on T lymphocyte subclasses. A sample of peripheral blood mononuclear leukocytes from a normal donor and a liver transplant recipient were isolated using density gradient centrifugation, cultured with PRA for 18 hours and incubated with monoclonal antibodies as described in "Detailed Description". Aliquots of the sample from each individual were incubated with either anti-IL2R-PE, anti-Leu-4-FITC and anti-IL2R-PE, anti-Leu3a-FITC and anti-IL2R-PE, or anti-Leu-2a-FITC and anti-IL2R-PE (Becton Dickinson, Mountain View, Calif.). Aliquots incubated with mouse-$IgG_1$-PE, or mouse-$IgG_1$-FITC and mouse-$IgG_1$-PE (Becton Dickinson, Mountain View, Calif.) served as controls to determine nonspecific binding. Four parameter data was collected on cells from each aliquot using an EPICS-V flow cytofluorometer (Coulter Corporation, Hialeah, Fla.) configured as described in "Detailed Description". Forward and orthogonal light scatter parameters were analyzed to determine if the cell was in a light scatter area of interest which substantially identified lymphocytes. Green and red fluorescence data analysis for aliquots incubated with two monoclonal antibodies was conducted as described in "Detailed Description". Fluorescence data analysis for aliquots incubated with only anti-IL2R-PE was similar, except that the minimal amount of IL2R expression was determined using simple one parameter (red fluorescence) subtraction from the fluorescence generated by the aliquot incubated with only mouse-$IgG_1$-PE.

Figure 13:
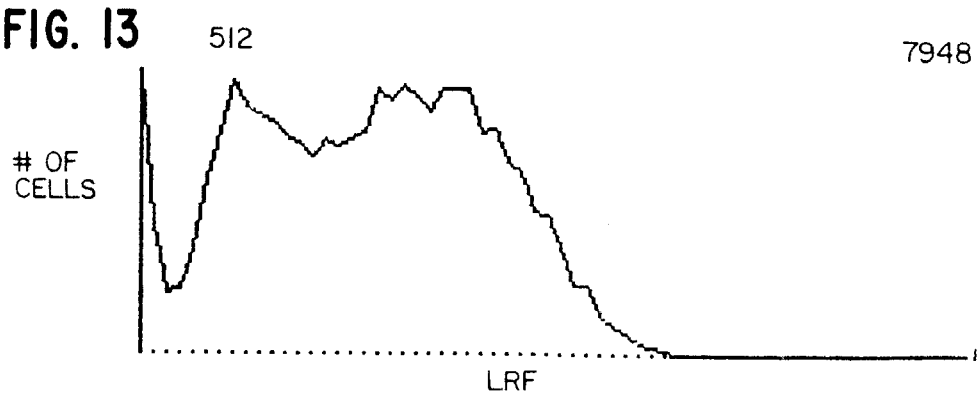
FIG. 13 shows a one parameter histogram of red fluorescence data (logarithmic scale) as measured by a flow cytofluorometer of stimulated mononuclear cells incubated with anti-IL2R-PE and determined to be lymphocytes similarly to FIG. 4.

The red fluorescence data relates to the number of "activated" lymphocytes. With respect to FIG. 13, this is a histogram wherein IL-2 receptors are measured on lymphocytes identified similarly as in FIG. 2 after the sample of mononuclear cells was cultured with PHA for 18 hours. The red fluorescent intensity relates to the number of excited fluorophores bound to the cell by the monoclonal antibody, anti-IL2R-PE. This figure was generated from an aliquot from the normal subject.

The results of this study are summarized in Table VIII.

TABLE VIII

| Subject | IL2R+* | Activated** Leu-4+ | Activated Leu-3a+ | Activated Leu-2a+ |
|---------|--------|--------------------|--------------------|-------------------|
| Normal | 49 | 61 | 65 | 9 |
| Liver Transplant Recipient A | 39 | 74 | 73 | 26 |

*Percentage of lymphocytes which expressed greater than the minimal IL-2 receptor density as determined by one parameter subtraction.
**Percentage of the antigenic determinant positive lymphocytes which express greater than the preset minimal IL-2 receptor density.

Example 5

This example shows analysis of activation antigen expression on particular monocluear cell subclasses after culturing with PHA for 18 hours. This analysis correlates with a known clinical assay, tritiated thymidine uptake after culturing with PHA 72 hours, however, yields more complete information concerning the immunoregulatory status of the mononuclear leukocyte immune system.

Samples of peripheral blood from a normal individual and a liver transplant recipient were isolated using density gradient centrifugation, cultured with PHA for 18 hours, incubated with monoclonal antibodies, four parameter data generated and analyzed as described in "Detailed Description".

The following results were obtained:

TABLE IX

| Subject | Biopsy Diagnosis Correlating With Sample | Tritiated Thymidine Uptake (72 hr Culture, PHA) | (18 hr. culture, PHA) | | |
|---------|---------|---------|---------|---------|---------|
| | | | Activated Leu-3a+* | % of Activated Leu-3a+ expressing a high density of IL2R | Activated Leu-2a+* |
| Normal | not done | 110,013 | 71 | 30 | 8 |
| Patient A | non-rejecting | 29,706 | 60 | 37 | 11 |
| Patient A | rejection | 211,867 | 73 | 39 | 26 |
| Patient A** | rejection | 170,953 | 66 | 10 | 39 |
| Patient A | rejection | 45,172 | 87 | 52 | 59 |

*Percentage of antigenic determinant positive lymphocytes which express greater than the preset minimal IL-2 receptor density.
**This sample was drawn about 2 hours after the patient had received his immunosuppressive medication.

From this study it can be seen that the present assay uses four parameter data analysis of stimulated mononuclear cells to obtain more detailed information concerning the immunoregulatory status of the mononuclear leukocyte immune system in less than 24 hours. The activation of lymphocyte subclasses after culturing with PHA for 18 hours is measured by determining the degree of IL-2 receptor activation antigen expression on these subclasses. Tritiated thymodine uptake is determined after a 72 hour culture with PHA. The results in Table IX illustrate the correlation of activated Leu-2a+ with rejection and percent of activated Leu-3a+ expressing a high density of IL-2 receptor with the acute effects of immunosupressive therapy during a rejection episode. This information can be more readily correlated with an altered immunoregulatory status than the tritiated thymidine uptake assay.

Data generation and analysis discussed in connection with the above embodiments of this assay can be conducted using the following apparatus. FIG. 14 is a stylized functional and structural representation of apparatus which may be used in accordance with the principles of the present invention to measure the four data parameters for each cell and to analyze this four parameter data to make a determination of the immunoregulatory status of the mononuclear leukocyte immune system. The apparatus is designed to yield an accurate and reproducible measurement of activation antigen expression on subclasses of mononuclear leukocytes.

As shown in FIG. 14, the apparatus consists of two major interrelated components and an interface module. The general design of the first component, a flow cytofluorometer (hereinafter FCFM), is known in the prior art and is briefly reviewed here.

An aliquot of a prepared sample, which has been isolated, cultured with a standard stimulus and incubated with specific monoclonal antibodies according to the methods presently disclosed, is received in machine intake port 97 for analysis. The sample cells flow through the flow system 105 including the flow chamber and channel 106 to the sensing zone 104 where each cell is illuminated with laser light from the laser 100 through the focusing lens system 102. As is known in the art, the cell sample stream is carried in laminar fashion within a flowing fluid sheath, to insure that a single cell will be illuminated in the sensing zone at a given time. Cells in liquid suspension are passed at a rapid rate (e.g. 2500 cells per second) through the sensing zone. Light is scattered to the forward light scatter photosensor 111 (e.g. photodiodes and amplifier) and to the orthogonal collection lens 107. The orthogonal collection lens is set orthogonal to both the direction of the cell sample stream and axis of laser light. Forward and orthogonal scattered light is collected in approximately a cone of half-angle 20 degrees. The electronic signal (hereinafter data signal) generated by the FLS photosensor is regulated by way of the control 132 (e.g., gain control for an amplifier) in the interface 130 which can be modified by a control signal from the microcomputer system 140.

Light which is collected in the lens 107 is split and filtered by the series of beam splitters and filters 109. An example of a combination of beam splitters and filters is described in the "Detailed Description" and is reiterated here as being exemplary, but not limiting, to the scope of the invention. Light of wavelength less than 488 nm is reflected by a 488 nm dichroic splitter and enters the photosensor 115 (e.g. photomultiplier tube with an associated preamplifier) which is regulated by the control 133 (e.g. an applied high voltage control for a photomultiplier tube) in the interface 130. In this example, this photosensor is used to detect orthogonal light scatter.

Light of wavelength greater than 488 nm is passed by the 488 dichroic splitter and continues along the orthogonal axis. The light passes a 515 nm interference long pass filter and a 560 nm dichroic splitter. Light of wavelength greater than 560 nm is reflected to a 590 nm long pass filter and enters photosensor 118 which is regulated by the control 134 in interface 130. Light of wavelength less than 560 nm is passed by the 560 nm dichroic splitter to a 525 nm band pass filter and enters the photosensor 120 which is regulated by the control 135 in the interface 130. In this example the photosensor 118 is used to detect red fluorescence and the photosensor 120 is used to detect green florescence. Each photosensor supplies an electronic output signal, i.e. data signal. The photosensor controls 133, 134, 135 can be modified by control signals from the microcomputer system 140.

In addition to photosensor controls, the interface contains other data signal processing elements, e.g. pulse detectors or integrators, which may be used, in accordance with the abilities of those with ordinary skill in the are, to produce data signals of suitable characteristics for subsequent processing. The interface 130 also includes the amplifiers 136, 137 and 138 to amplify the data signal which is then supplied to the microcomputer system 140. In a preferred embodiment, these are logarithmic amplifiers. The interface contains the control signal lines 160, including the control signal lines to the FCFM to control the laser 100 and the flow chamber and channel 106. By containing all important control and data signal processing elements, the interface facilitates maintenance and corrective servicing of the apparatus.

The microcomputer system 140 consists of a central processing unit, memory, a terminal for operator interface, a data storage device, A to D converters for the incoming data signals on the data signal lines 150, D to A converters for the outgoing control signals on the control signal lines 160 and the software to analyze the data signals and to ensure the accuracy and reproducibility of the measurements made by the FCFM 98. The system's software contains routines to perform the following functions: four parameter data storage for each cell within threshold ranges pertinent to the analysis, analysis of light scatter data parameters to determine the class of each cell, compensation of fluorescence data parameters of each cell for the overlap of the emission spectra of different fluorophores, analysis of the compensated fluorescence data parameters to determine the subclass and activation antigen density of each cell of a specified class, analysis of the degree of activation for each subclass to make a determination of the immunoregulatory status, report output, FCFM control, operator interface and system integration/operation.

The system controller routine ensures the proper integration of the other software routines and overall operation of the system, including the storage and retrieval of data from the storage device. It is substantially a disk operating system as is known in the art, with modifications pertinent to this method and apparatus. The system controller routine communicates with the operator of the apparatus to accept data concerning the aliquot of the patient sample to be analyzed, this can include clinical data about the patient.

The storage routine will process the incoming data signals to determine if the light scatter parameters of a cell are within threshold ranges set by the operator and store the four parameter data for that cell.

The light scatter analysis routine will determine the class for each cell stored using preset areas of interest identifying certain classes. In a preferred embodiment, forward and orthogonal light scatter are used to make class determinations. If the cell is determined to be in an operator-specified class, further analysis is performed by the compensation and fluorescence analysis routines.

For those cells in a specified class as indicated by the light scatter analysis routine, the compensation routine corrects the fluorescence data parameters of the cell for the overlap of the emission spectra of the fluorophores which were conjugated to the monoclonal antibodies. In a preferred embodiment, the percentages are preset and determined by the iterative process described in the "Detailed Description". The compensated fluorescence parameter data are then passed to the fluorescence analysis routine. In an alternative embodiment, the compensation routine could be implemented with hardware as has been done in the prior art.

The fluorescence analyzer collects the compensated fluorescence parameter data for all cells of a specified class as indicated by the light scatter analysis routine. This routine identifies the subclass, enumerates the cells in the subclass and those cells in the subclass which are activated. This collected data is referred to as cumulative data and can be represented by histograms. In a preferred embodiment as described in the "Detailed Description", a histogram of the amount of fluorescence indicative of antigenic determinants on the cell is generated. The channel number, on the histogram, representing the x-intercept of an approximation of the tangent to the positive slope of the curve generated is used as the minimal density necessary for a cell to qualify as a member of the specified subclass. A similar procedure can be used to determine the maximal antigenic determinant density from the negative slope of the curve generated, alternatively, a default value set at the highest density measurable can be used. The cumulative data is then analyzed using these density boundaries to enumerate cells which are positive for the antigenic determinant and can be assigned to the subclass. Using the channel number indicative of cellular activation determined by the iterative process as described in the "Detailed Description", the activated cells belonging to the subclass are enumerated. Also, a range can be specified such that cells belonging to the subclass and having activation antigen expression within the range can be enumerated. The fluorescense analyzer can also monitor the degree of antigenic determinant modulation with activation or enumerate cells with two specific antigenic determinants of known densities. An alternative within the scope of this invention is an additional, orthogonally placed photosensor with a data signal conveying information on a third wavelength of fluorescence to be used to identify distinct antigenic determinants. This alternative can include an additional laser with an associated focusing lens system and delay circuit for any other signal processing elements associated with the additional photosensor, as is known in the art.

Analysis of the degree of activation for each subclass to assess the immunoregulatory status is done by the statistical analyzer routine. The statistical analyzer routine receives information from the fluorescence analysis routine concerning class, quantity of cells in the subclass, quantity of activated cells in the subclass and other determinations, e.g. quantity of cells in the subclass expressing activation antigen within a certain range. The statistical analyzer routine uses this information to determine the level of activation, e.g. percentage of a subclass which is activated, percentage of activated cells in a subclass expressing activation antigens at a high density, ratios of activated subclasses, combinations of these determinations, etc. (For illustrations, see the Examples above.)

The report output routine generate a report with the assessment of the immunoregulatory status as determined by the statistical analyzer routine. The report can contain averaged results for normal individuals or patients similar to the one analyzed for further assessment by the clinician.

To ensure accuracy and reproducibility of the measurements made by the FCFM 98 and therefore the results produced by the apparatus, uniformly shaped control spheres with a predetermined quantity of fluorophores bound to their surfaces can be analyzed by the apparatus. The values of the four parameter data for these spheres are predetermined. Therefore, the light scatter and fluorescence analysis routines can collect data on an aliquot of a sample of control spheres. The mean value for each parameter can be determined from this cumulative four parameter data and sent to the FCFM control routine. The FCFM control routine compares these values with the predetermined values. Adjustments of the FCFM 98 and photosensor controls can be made by generating control signals such that accurate and reproducible measurements are made. This often involves an iterative process of rerunning the control spheres until there is no significant deviation from the predetermined values. This facilitates the establishment of preset areas of interest to be used to process patient samples. It should be noted that by including the control spheres in the aliquot of cells at a known concentration, analysis of these spheres while data is being collected on the cells can assist in flow system clog detection.

The FCFM control routine also controls the operation of the FCFM 98 per the instructions of the system controller routine.

The applications of this apparatus include, but are not limited to, the Examples described above. The apparatus ensures the accuracy, reproducibility and timeliness of the results of the assay, these being necessary to assist in the clinical diagnostic and therapeutic decision process. Also, the ability to detect clogs in the flow system assists in ensuring that there is minimal loss of the clinical sample.

It is to be understood that the schematics of FIG. 14 are merely representative of the functional aspects of the principles of the present invention, and may be embodied in numerous alternative fashions in accordance with the abilities of one of ordinary skill in the art.

What is claimed is:

1. A method for assessing an alteration of the in vivo immunoregulatory status of a mammal comprising:
   (a) culturing a sample of peripheral mononuclear cells from a mammal with a standard stimulus for up to 24 hours;
   (b) measuring an aliquot of said cultured sample for the percentage of at least one subclass of mononuclear cells expressing activation antigen in vitro; and
   (c) comparing said percentage with a predetermined level of said percentage as an indicator of an alteration of the in vivo immunoregulatory status of said mammal.

2. The method of claim 1 wherein said activation antigen is IL2R.

3. The method of claim 1 wherein said subclass of mononuclear cells is natural killer cells.

4. The method of claim 1 wherein said subclass of mononuclear cells is helper/inducer T lymphocytes.

5. The method of claim 1 wherein said subclass of mononuclear cells is suppressor/cytotoxic T lymphocytes.

6. The method of claim 1 wherein said subclass of mononuclear cells is suppressor T lymphocytes.

7. The method of claim 1 wherein said subclass of mononuclear cells is cytotoxic T lymphocytes.

8. The method of claim 1 wherein said subclass of mononuclear cells is helper T lymphocytes.

9. The method of claim 1 wherein said subclass of mononuclear cells is inducer T lymphocytes.

10. The method of claim 1 wherein said mammal is patient.

11. The method of claim 1 wherein said predetermined level is obtained from culturing a sample of peripheral mononuclear cells from a mammal with a standard stimulus for up to 24 hours and measuring said cultured sample for the percentage of at least one subclass of mononuclear cells expressing activation antigen in vitro.

12. The method of claim 1 wherein said predetermined level is obtained from previously culturing a sample of peripheral mononuclear cells from said mammal and measuring said cultured sample for the percentage of at least one subclass of mononuclear cells expressing activation antigen in vitro.

13. The method of claim 1 wherein said predetermined level is obtained from culturing a sample of peripheral mononuclear cells from a mammal who has an immune-mediated disorder and measuring said cultured sample for the percentage of at least one subclass of mononuclear cells expressing activation antigen in vitro.

14. The method of claim 1 wherein said predetermined level is obtained from culturing a sample of peripheral mononuclear cells from a mammal who has received an immunomodulating agent in vivo, and measuring said cultured sample for the percentage of at least one subclass of mononuclear cells expressing activation antigen in vitro.

15. The method of claim 1 wherein measuring said subclass is performed using at least one fluorophore-conjugated monoclonal antibody.

16. The method of claim 1 wherein measuring said activation antigen is performed using at least one fluorophore-conjugated monoclonal antibody.

17. The method of claim 1 wherein the culturing of the sample of mononuclear cells from a mammal with a standard stimulus for up to 24 hours is performed without the in vitro addition of an immunomodulating agent.

* * * * *